United States Patent
Maeyama et al.

(10) Patent No.: US 8,903,040 B2
(45) Date of Patent: Dec. 2, 2014

(54) X-RAY MULTIPLE SPECTROSCOPIC ANALYZER

(75) Inventors: Masataka Maeyama, Ome (JP); Akihito Yamano, Tokyo (JP)

(73) Assignee: Rigaku Corporation (JP)

( * ) Notice: Subject to any disclaimer, the term of this patent is extended or adjusted under 35 U.S.C. 154(b) by 281 days.

(21) Appl. No.: 13/463,980

(22) Filed: May 4, 2012

(65) Prior Publication Data

US 2012/0288058 A1    Nov. 15, 2012

(30) Foreign Application Priority Data

May 13, 2011 (JP) .................................. 2011-108382
Mar. 23, 2012 (JP) .................................. 2012-68128

(51) Int. Cl.
*G01N 23/223* (2006.01)
*G01N 23/207* (2006.01)
*G01N 23/22* (2006.01)

(52) U.S. Cl.
CPC ............ *G01N 23/207* (2013.01); *G01N 23/223* (2013.01); *G01N 23/2206* (2013.01)
USPC .................. 378/46; 378/45; 378/73; 378/79; 378/81

(58) Field of Classification Search
CPC ............ G01N 23/20; G01N 23/20008; G01N 23/20083; G01N 23/207; G01N 23/2076; G01N 23/2206; G01N 23/223
USPC .................... 378/44, 45, 6, 71, 73, 79, 81, 46
See application file for complete search history.

(56) References Cited

U.S. PATENT DOCUMENTS

| | | | | |
|---|---|---|---|---|
| 5,640,437 A | * | 6/1997 | Grueninger | 378/79 |
| 5,745,543 A | * | 4/1998 | De Bokx et al. | 378/45 |
| 2003/0002620 A1 | * | 1/2003 | Mazor et al. | 378/49 |
| 2006/0165218 A1 | * | 7/2006 | Uda | 378/71 |
| 2010/0150307 A1 | * | 6/2010 | Grodzins | 378/45 |

FOREIGN PATENT DOCUMENTS

| | | |
|---|---|---|
| JP | 5-188019 A | 7/1993 |
| JP | 9-257726 A | 10/1997 |
| JP | 11-14566 A | 1/1999 |

* cited by examiner

*Primary Examiner* — Glen Kao
(74) *Attorney, Agent, or Firm* — Cantor Colburn LLP

(57) ABSTRACT

An X-ray multiple spectroscopic analyzer includes an X-ray source, an optical system inputting X-rays to a single-crystal sample, a sample stage supporting the single-crystal sample, an X-ray diffraction detector, a rotation driving system that changes the angle of the X-ray diffraction detector, an X-ray diffraction measurement data storage unit, a structural analysis data analyzing unit, an energy-dispersive X-ray fluorescence detector, an X-ray fluorescence measurement data storage unit, an X-ray fluorescence analyzing unit, an X-ray fluorescence analysis data storage unit, and X-ray fluorescence analysis data acquiring unit. The structural analysis data analyzing unit analyzes the data of the crystal structure further on the basis of the analysis data of the fluorescent X-rays output from the X-ray fluorescence analysis data acquiring unit.

12 Claims, 12 Drawing Sheets

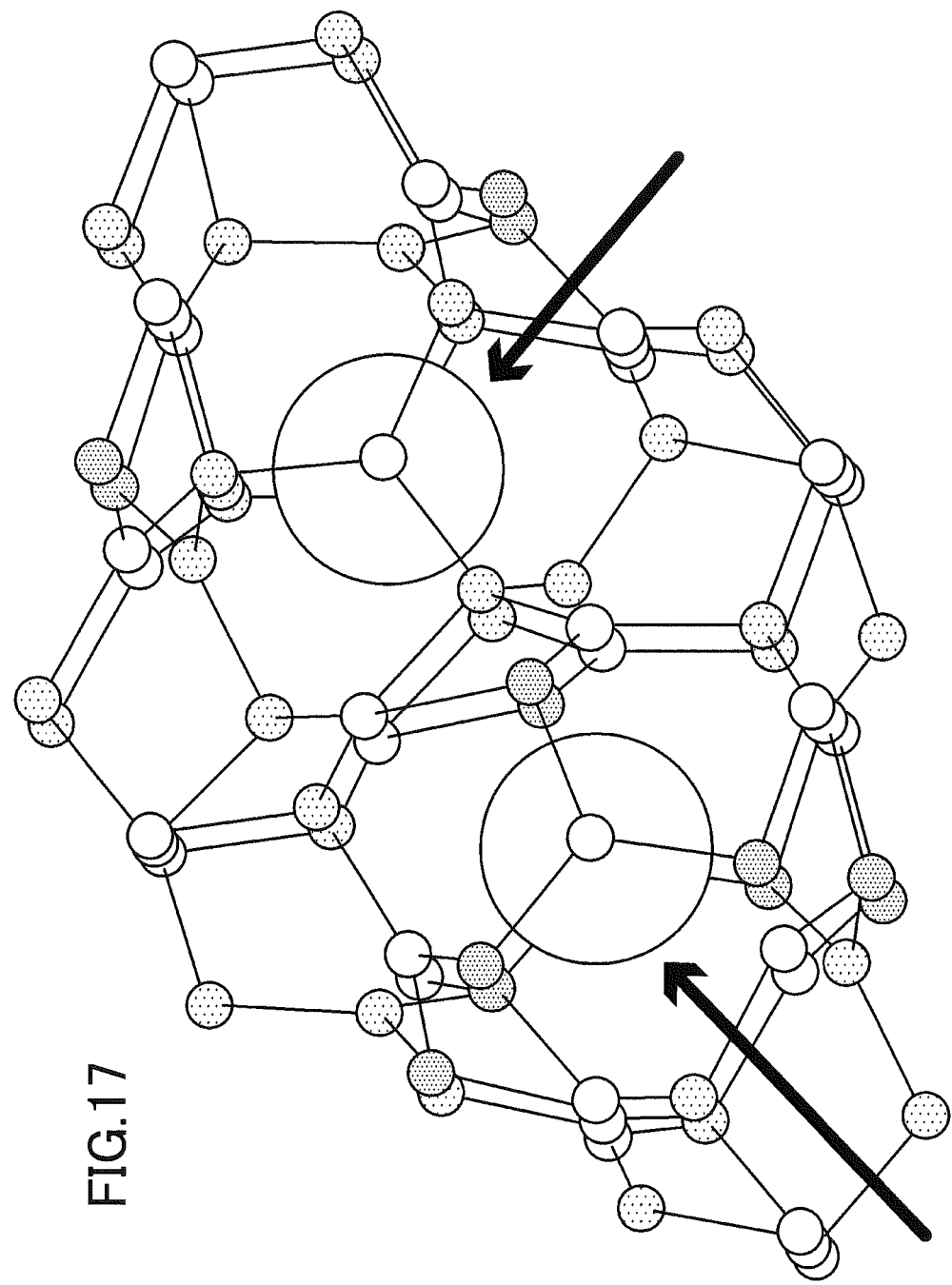

X-RAY MULTIPLE SPECTROSCOPIC ANALYZER

CROSS-REFERENCE TO RELATED APPLICATION

The present application claims priority from Japanese applications JP 2011-108382, filed on May 13, 2011 and JP 2012-68128, filed on Mar. 23, 2012, the content of which is hereby incorporated by reference into this application.

BACKGROUND OF THE INVENTION

1. Field of the Invention

The present invention relates to an X-ray spectroscopic analyzer that analyzes a single-crystal structure through the use of both X-ray diffraction analysis and energy-dispersive X-ray fluorescence analysis.

2. Description of the Related Art

In an X-ray diffractometer, a diffraction pattern of a sample is obtained by irradiating the sample with X-rays and measuring X-ray diffraction generated from the sample. For example, when the sample is a single crystal, the crystal structure is mainly analyzed using measurement data of diffraction patterns. On the other hand, in an X-ray fluorescence spectrometer, element information of a sample is obtained by irradiating a sample with X-rays and measuring X-ray fluorescence radiated from the sample. That is, atoms are specified from the measured X-ray fluorescence and the contents of the atoms are obtained from peak intensities of the X-ray fluorescence.

In single-crystal structure analysis, in addition to measurement data of a diffraction pattern of the single-crystal sample acquired through the use of the X-ray diffractometer, element information of a single-crystal sample, particularly, information of a heavy element, acquired through the use of the X-ray Fluorescence Spectrometer plays a very important role in determining phase information necessary for analyzing a three-dimensional crystal structure.

In order to cope with the speed of recent development, it is necessary to raise the analyzing speed using both analysis results as quickly as possible and there is a demand for precise analysis results. In order to achieve a high measuring speed and high accuracy, there is a demand for an environment in which measurement data of a diffraction pattern acquired through X-ray diffraction analysis and element information acquired through X-ray fluorescence analysis can be used as information to ease single-crystal structure analysis through the use of an X-ray spectroscopic analyzer which can perform both the X-ray diffraction analysis and the X-ray fluorescence analysis using a single apparatus.

SUMMARY OF THE INVENTION

Techniques of performing both the X-ray diffraction analysis and the X-ray fluorescence analysis using a single apparatus have been suggested. JP11-14566 A discloses a technique of moving an X-ray fluorescence detector with movement in angle of an X-ray diffraction detector. JP9-257726 A discloses a technique in which a dispersive crystal is disposed in a θ-rotation driving system of a goniometer, an X-ray fluorescence analyzing attachment is disposed in a 2θ-rotation driving system of the goniometer, and the dispersive crystal and the X-ray fluorescence analyzing attachment are moved with the movement in angle of the X-ray detector measuring the diffraction of X-rays. The X-ray fluorescence analysis disclosed in JP9-257726 A is wavelength-dispersive X-ray analysis (hereinafter, referred to as WDX) in which X-rays are dispersed with a dispersive crystal. JP5-188019 A discloses an X-ray multiple spectroscopic analyzer which can analyze the same place of a thin film, a surface of the thin film, an interface, and the like in a comprehensive manner by analyzing the X-ray diffraction and the X-ray fluorescence of a sample and measuring fluorescent EXAFS using X-rays as a probe.

A single-crystal sample used for X-ray diffraction measurement for X-ray single-crystal structure analysis is a small sample with a size of, for example, 100 μm or less. When the single-crystal sample is irradiated with X-rays from an X-ray source used for X-ray diffraction measurement, the X-ray fluorescence analysis based on the WDX having small intensity of fluorescent X-rays radiated from the single-crystal sample and having a high resolution can be preferably used.

On the other hand, in an X-ray diffractometer used for the X-ray single-crystal structure analysis, it is necessary to provide a rotation driving system to a sample stage supporting a single-crystal sample in order to perform complicated rotation movement of the single-crystal sample and the space in which an X-ray detector measuring fluorescent X-rays is disposed in the vicinity of the single-crystal sample is severely limited.

Accordingly, in the X-ray diffractometer employing the technique disclosed in JP11-14566 A and performing the X-ray single-crystal structure analysis, it is difficult to dispose an X-ray fluorescence detector and a parallel linking mechanism shown in FIG. 1 of JP11-14566 A in the vicinity of the single-crystal sample. Although the X-ray fluorescence analysis based on the WDX is preferable, it is difficult to dispose the dispersive crystal and the X-ray fluorescence analyzing attachment in the X-ray diffractometer which performs the X-ray single-crystal structure analysis and to move the attachment with the movement in angle of the rotation driving system of the X-ray diffractometer, by applying the technique disclosed in JP9-257726 A. Structures such as the dispersive crystal and the goniometer in addition to the X-ray detector are required for the X-ray fluorescence analysis based on the WDX and it is more difficult to dispose the structures in the X-ray diffractometer which can be disposed in the vicinity of the single-crystal sample and which is limited in space. It is also difficult to apply the technique disclosed in JP5-188019 A, which is different in structure from the X-ray diffractometer, to the X-ray diffractometer which performs the X-ray single-crystal structure analysis.

Therefore, although there are related arts regarding the X-ray spectroscopic analyzers including X-ray diffraction analysis, X-ray fluorescence analysis, EXAFS, and the like, a single apparatus to perform both the X-ray diffraction analysis and the X-ray fluorescence analysis for the single-crystal structure analysis has not been suggested.

In the X-ray single-crystal structure analysis, element information is important in determining a phase for analyzing a three-dimensional crystal structure. Nevertheless, the X-ray diffraction measurement and the X-ray fluorescence measurement for the X-ray single-crystal structure analysis are currently performed by different devices and two devices are necessary, thereby causing a problem of an increase in cost. There is also a problem in that the measurement time increases because the X-ray diffraction measurement and the X-ray fluorescence measurement are separately performed on the same single-crystal sample. When the single-crystal sample is an unstable sample, particularly, two measurements are performed by different devices and thus the sample is deteriorated due to the increase in measurement time or transfer of the single-crystal sample, thereby making the analysis more difficult. The element information acquired through the X-ray fluorescence analysis has to be transmitted to the software performing the single-crystal structure analysis, which increases difficulty.

The invention is made in consideration of these problems and an object thereof is to provide an X-ray spectroscopic analyzer which can analyze a single-crystal structure through the use of both the X-ray diffraction analysis and the X-ray fluorescence analysis.

(1) According to a first aspect of the invention, there is provided an X-ray multiple spectroscopic analyzer including: an X-ray source that radiates X-rays; an optical system that inputs the X-rays radiated from the X-ray source to a single-crystal sample; a sample stage that supports the single-crystal sample, with one or more rotation driving systems that rotate the single-crystal sample; an X-ray diffraction detector that detects diffracted X-rays generated from the single-crystal sample; a rotation driving system that changes the angle of the X-ray diffraction detector with respect to the single-crystal sample; an X-ray diffraction measurement data storage unit that stores measurement data of the diffracted X-rays detected by the X-ray diffraction detector; a structural analysis data analyzing unit that analyzes data of a crystal structure on the basis of the measurement data of the diffracted X-rays stored in the X-ray diffraction measurement data storage unit; an energy-dispersive X-ray fluorescence detector that detects fluorescent X-rays radiated from the single-crystal sample; an X-ray fluorescence measurement data storage unit that stores measurement data of the fluorescent X-rays detected by the energy-dispersive X-ray fluorescence detector; an X-ray fluorescence analyzing unit that analyzes the fluorescent X-rays on the basis of the measurement data of the fluorescent X-rays stored in the X-ray fluorescence measurement data storage unit; an X-ray fluorescence analysis data storage unit that stores analysis data of the fluorescent X-rays output from the X-ray fluorescence analyzing unit; and X-ray fluorescence analysis data acquiring unit for acquiring the analysis data of the fluorescent X-rays stored in the X-ray fluorescence analysis data storage unit and outputting the acquired X-ray fluorescence analysis data to the structural analysis data analyzing unit, wherein the structural analysis data analyzing unit analyzes the data of the crystal structure further on the basis of the analysis data of the fluorescent X-rays output from the X-ray fluorescence analysis data acquiring unit.

(2) The X-ray multiple spectroscopic analyzer set forth in (1), may further include a beam stopper that is disposed opposite to the optical system about the single-crystal sample and that blocks a direct beam of X-rays input to the single-crystal sample from the optical system, and the energy-dispersive X-ray fluorescence detector may include a light-receiving portion that receives the detected X-rays and an X-ray blocking member that is disposed between the beam stopper and the light-receiving portion and that blocks fluorescent X-rays radiated from a part of the beam stopper which is directly irradiated with the direct beam.

(3) In the X-ray multiple spectroscopic analyzer set forth in (2), the X-ray blocking member may surround the peripheral edge of the light-receiving portion.

(4) In the X-ray multiple spectroscopic analyzer set forth in (3), the X-ray blocking member may have a tip formed in a tapered shape.

(5) In the X-ray multiple spectroscopic analyzer set forth in (3), the X-ray blocking member may include a hollow light-guiding tube therein and functions as a poly-capillary.

(6) In the X-ray multiple spectroscopic analyzer set forth in one of (1) to (5), the light-receiving portion of the energy-dispersive X-ray fluorescence detector may be disposed on the optical system side about a plane perpendicular to the optical axis of a direct beam of X-rays input to the single-crystal sample from the optical system and passing through the single-crystal sample.

(7) In the X-ray multiple spectroscopic analyzer set forth in one of (1) to (6), the energy-dispersive X-ray fluorescence detector may further include a retreating mechanism that can retreat outward from the single-crystal sample.

(8) In the X-ray multiple spectroscopic analyzer set forth in one of (1) to (7), the energy dispersive X-ray fluorescence detector may detect a posture where the sample stage supports the single-crystal sample by detecting the fluorescent X-rays radiated from the single-crystal sample.

(9) In the X-ray multiple spectroscopic analyzer set forth in one of (1) to (8), the energy dispersive X-ray fluorescence detector may be a silicon drift detector or a lithium-drift silicon detector.

(10) In the X-ray multiple spectroscopic analyzer set forth in one of (1) to (9), the energy dispersive X-ray fluorescence detector may detect the fluorescent X-rays radiated from the single-crystal sample in a first period which is a partial period of a period in which the X-ray diffraction detector detects the diffracted X-rays generated from the single-crystal sample.

(11) In the X-ray multiple spectroscopic analyzer set forth in one of (1) to (6), the X-ray fluorescence analyzing unit may analyze the fluorescent X-rays on the basis of the measurement data of the fluorescent X-rays, which is detected by the energy dispersive X-ray fluorescence detector in the first period, in a second period which is a partial period of the period in which the X-ray diffraction detector detects the diffracted X-rays generated from the single-crystal sample and which is subsequent to the first period.

(12) In the X-ray multiple spectroscopic analyzer set forth in one of (1) to (11), when a predetermined atom included in a compound constituting the single-crystal sample has a possibility of plural kind of atoms, the structural analysis data analyzing unit may determine the predetermined atom from the analysis data of the fluorescent X-rays and may determine the crystal structure of the single-crystal sample on the basis of the determined atom.

(13) In the X-ray multiple spectroscopic analyzer set forth in one of (1) to (11), when a part of a predetermined kind of atoms included in a compound constituting the single-crystal sample are substituted with a different kind of atoms, the structural analysis data analyzing unit may determine an amount of the different atom from the analysis data of the fluorescent X-rays and may determine the crystal structure of the single-crystal sample on the basis of the substituted amount.

According to the aspect of the invention, it is possible to provide an X-ray spectroscopic analyzer which can analyze a single-crystal structure through the use of both X-ray diffraction analysis and X-ray fluorescence analysis.

BRIEF DESCRIPTION OF THE DRAWINGS

FIG. 17 is a diagram illustrating an example of the structure of a molecule model of a compound which is subjected to single-crystal structure analysis according to a fourth embodiment of the invention.

DETAILED DESCRIPTION OF THE INVENTION

Figure 1:
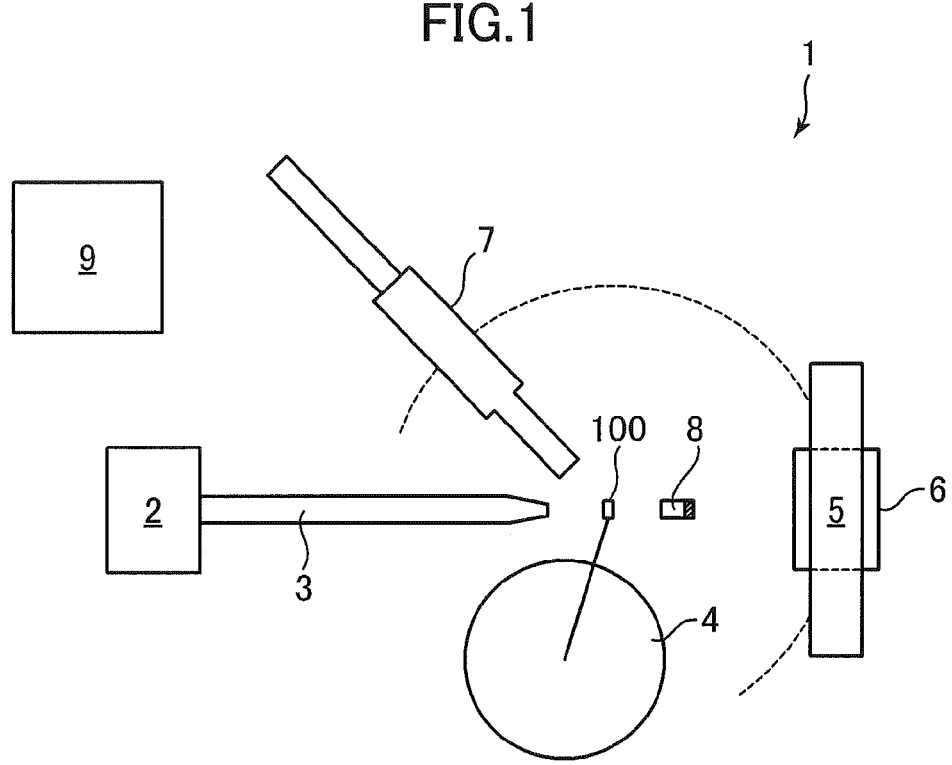
FIG. 1 is a diagram schematically illustrating the structure of an X-ray multiple spectroscopic analyzer according to a first embodiment of the invention.

Hereinafter, exemplary embodiments of the invention will be described in detail with reference to the accompanying drawings. Here, the drawings described below are intended to show examples of the embodiments and the scales in the drawings are not necessarily identical to the scales described in the examples.

First Embodiment

FIG. 1 is a diagram schematically illustrating the structure of an X-ray multiple spectroscopic analyzer 1 according to a first embodiment of the invention. The X-ray multiple spectroscopic analyzer 1 according to this embodiment is an X-ray multiple spectroscopic analyzer which can perform both X-ray diffraction analysis and X-ray fluorescence analysis on a single-crystal sample 100 and can analyze a single-crystal structure. The X-ray multiple spectroscopic analyzer 1 includes an X-ray source 2 radiating X-rays, an optical system 3 inputting the X-rays radiated from the X-ray source 2 to the sample 100, a sample stage 4 supporting the sample 100, an X-ray diffraction detector 5 detecting diffracted X-rays generated from the sample 100, a rotation driving system 6 changing the angle of the X-ray diffraction detector 5 with respect to the sample 100, an X-ray fluorescence detector 7 (energy-dispersive X-ray fluorescence analyzer) for energy-dispersive X-ray analysis (hereinafter, referred to as "EDX"), a beam stopper 8, and a control and analysis unit 9 controlling X-ray diffraction measurement and X-ray fluorescent measurement and analyzing measurement data. The X-ray multiple spectroscopic analyzer 1 further includes a sample cooling unit 10 (not shown). The sample cooling unit 10 is disposed above the sample 100 and the sample cooling unit 10 can spray cooling nitrogen gas to the sample 100 to maintain the sample 100 at a predetermined temperature.

The X-ray multiple spectroscopic analyzer 1 according to this embodiment is characterized in that an X-ray diffractometer capable of analyzing a single-crystal structure and an X-ray fluorescence spectrometer using an X-ray fluorescence detector for EDX are provided to a single apparatus. Accordingly, an X-ray multiple spectroscopic analyzer capable of performing both X-ray diffraction analysis and X-ray fluorescence analysis necessary for analysis of a single-crystal structure is implemented. Since a crystal of a single-crystal sample used for analysis of a single-crystal structure is small as described above and fluorescent X-rays radiated from the single-crystal sample is weak, it is thought that it is difficult to detect fluorescent X-rays through the use of the X-ray fluorescence detector for EDX, but the inventors experimentally found that it is possible. Accordingly, it is possible to perform both analyses of the X-ray diffraction analysis and the X-ray fluorescence analysis using a single apparatus.

The constitution of the X-ray multiple spectroscopic analyzer 1 according to this embodiment will be described below. The X-ray source 2 includes an X-ray tube and radiates X-rays by heating thermal electrons emitted from a cathode to collide with a target. The optical system 3 is disposed to input the X-rays radiated from the X-ray source 2 to the sample 100. The optical system 3 includes a multi-layered focusing optics and a collimator and concentrates the X-rays radiated from the X-ray source 2 through the use of the multi-layered focusing optics and outputs the X-rays to the sample 100 through the collimator. Here, the combination of the X-ray source 2 and the optical system 3 is referred to as an "X-ray generating unit". Strong X-rays directly emitted from the X-ray generating unit and input to the sample 100 are referred to as a direct beam of X-rays. The X-ray generating unit can emit high-luminance X-rays of which the X-ray dose per unit area is 10 kW/mm$^2$. Here, the structure of the X-ray generating unit is not limited to the above-mentioned structure.

The sample stage 4 includes a needle-like sample holder and one or more rotation driving systems. The single-crystal sample 100 is mounted on the tip of the needle-like sample holder and the sample 100 is supported by the sample holder. The sample holder is disposed so that the direct beam of X-rays emitted from the X-ray generating unit is input to the sample 100. The other end of the sample holder is fixed to the rotation driving system and the sample 100 can be three-dimensionally rotated by the use of the rotation driving system(s). In measurement of X-ray diffraction, even when the sample 100 is rotated in any direction by the rotation driving system(s), the sample 100 is completely bathed in the direct beam of X-rays.

The X-ray diffraction detector 5 is, for example, a CCD (Charge Coupled Device). The sample 100 is irradiated with the direct beam of X-rays and diffracted X-rays are generated from the sample 100. When it is disposed opposite to the X-ray generating unit about the sample 100, the X-ray diffraction detector 5 is disposed perpendicular to the optical axis of the direct beam of X-rays and can detect the diffracted X-rays in a two-dimensional plane. The X-ray diffraction detector 5 is disposed on the rotation driving system 6 of which the angle can be changed about the sample 100. The X-ray diffraction detector 5 can detect the whole diffraction pattern of the sample 100 by the use of the rotation driving system(s) of the sample stage 4 and the rotation driving system 6. The X-ray diffraction detector 5 is not limited to the CCD, but any X-ray detector can be used as long as it can detect the diffraction pattern of the single-crystal sample 100.

As described above, the X-ray fluorescence detector 7 is an X-ray detector for EDX and is, for example, an SDD (Silicon Drift Detector). The X-ray fluorescence detector 7 can detect fluorescent X-rays radiated from the sample 100. The X-ray fluorescence detector 7 includes a light-receiving portion 12 (not shown) as described later. The light-receiving portion 12 is a portion receiving the fluorescent X-rays detected by the X-ray fluorescence detector 7 and has a light-receiving surface. The fluorescent X-rays received by the light-receiving portion 12 enter the inside of the body of the X-ray fluorescence detector 7 through the light-receiving portion 12 and are converted into electrical signals, whereby the X-ray fluorescence detector 7 can detect the fluorescent X-rays. Here, the X-ray fluorescence detector 7 employs the SDD, but is not limited thereto, as long as the X-ray detector is an X-ray detector for EDX capable of measuring the fluorescent X-rays radiated from the sample 100 and is small enough to dispose. For example, a Si (Li) type detector (lithium drift silicon detector) can measure the fluorescent X-rays radiated from the sample 100 and can be applied to the invention.

The beam stopper 8 is disposed in the optical axis of the direct beam of X-rays and on the opposite side of the X-ray generating unit (the optical system 3) about the sample 100. The beam stopper 8 blocks the direct beam of X-rays emitted from the X-ray generating unit and input to the sample 100. Accordingly, the beam stopper 8 prevents the direct beam of X-rays from reaching the X-ray diffraction detector 5, thereby preventing damage to the X-ray diffraction detector 5. The beam stopper 8 is mounted on an arm supporting the beam stopper 8 and the arm is fixed to the X-ray generating unit. Accordingly, even when the rotation driving system(s) of the sample stage 4 inclines the sample 100 in any direction and even when the rotation driving system 6 moves the X-ray diffraction detector 5 to any position, the beam stopper 8 prevents the direct beam of X-rays from traveling to the front from the beam stopper 8 in the emission direction of the direct beam of X-rays in the optical axis of the direct beam of X-rays.

The control and analysis unit 9 controls the measurement of X-ray diffraction and the measurement of X-ray fluorescence and analyzes the acquired measurement data. Depending on the control method, only the X-ray diffraction may be measured, only the X-ray fluorescence may be measured, or both the X-ray diffraction and the X-ray fluorescence may be measured. In the measurement of the X-ray diffraction, the control and analysis unit 9 controls the driving of the rotation driving system(s) of the sample stage 4 and the rotation driving system 6 having the X-ray diffraction detector 5 disposed thereon, controls the detection of the X-ray diffraction detector 5, and collects plural pieces of information on a diffraction pattern detected by the X-ray diffraction detector 5, thereby acquiring all the measurement data of the diffraction pattern. In the measurement of the X-ray fluorescence, the control and analysis unit 9 controls the detection of the X-ray fluorescence detector 7 to acquire the measurement data of the X-ray fluorescence.

Figure 2:
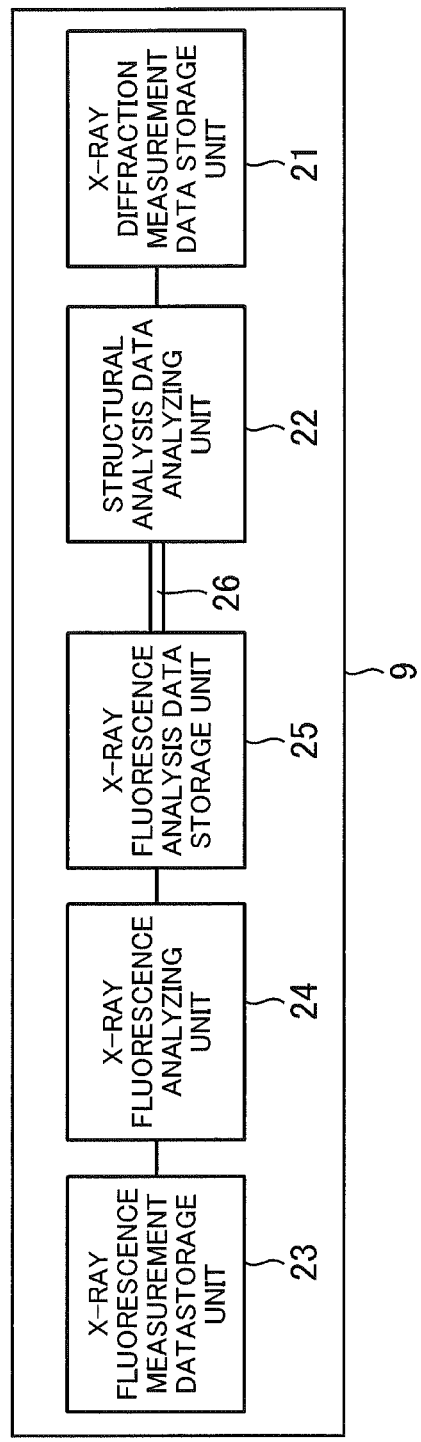
FIG. 2 is a block diagram illustrating the structure of a control and analysis unit according to the first embodiment of the invention.

FIG. 2 is a block diagram illustrating the control and analysis unit 9 according to this embodiment. Means for storing and analyzing data in the control and analysis unit 9 is mainly shown therein. The control and analysis unit 9 includes an X-ray diffraction measurement data storage unit 21, a structural analysis data analyzing unit 22, an X-ray fluorescence measurement data storage unit 23, an X-ray fluorescence analyzing unit 24, an X-ray fluorescence analysis data storage unit 25, and X-ray fluorescence analysis data acquiring unit 26 (X-ray fluorescence analysis data acquiring means).

The X-ray diffraction measurement data storage unit 21 stores the diffracted X-rays detected by the X-ray diffraction detector as measurement data of the diffracted X-rays. Here, the measurement data of the diffracted X-rays of the sample 100 includes, for example, a diffraction position and intensity of a diffraction pattern of the sample 100. Here, the diffraction position corresponds to a reciprocal lattice space index (hkl). The structural analysis data analyzing unit 22 includes means for acquiring the measurement data of the diffracted X-rays stored in the X-ray diffraction measurement data storage unit 21 and analyzes the data of the single-crystal structure of the sample 100 on the basis of the measurement data of the diffracted X-rays and the like. The X-ray fluorescence measurement data storage unit 23 stores the measurement data of the fluorescent X-rays radiated from the sample 100 and detected by the X-ray fluorescence detector 7. The measurement data of the fluorescent X-rays includes, for example, plural energy values depending on the resolution and intensity of the fluorescent X-rays at the corresponding energy value. A fluorescent X-ray spectrum can be displayed from the measurement data of the fluorescent X-rays. The X-ray fluorescence analyzing unit 24 includes means for acquiring the measurement data of the fluorescent X-rays stored in the X-ray fluorescence measurement data storage unit 23 and analyzes the fluorescent X-rays on the basis of the measurement data of the fluorescent X-rays. The X-ray fluorescence analyzing unit 24 analyzes element information such as an element included in the sample 100 and the contents of the element on the basis of the peak energy and the peak intensity of the fluorescent X-ray spectrum of the sample 100. The X-ray fluorescence analyzing unit 24 outputs the element information of the sample 100 to the X-ray fluorescence analysis data storage unit 25 as the X-ray fluorescence analysis data. The X-ray fluorescence analysis data storage unit 25 stores the X-ray fluorescence analysis data output from the X-ray fluorescence analyzing unit 24. The X-ray fluorescence analysis data acquiring unit 26 acquires the X-ray fluorescence analysis data stored in the X-ray fluorescence analysis data storage unit 25 and outputs the X-ray fluorescence analysis data to the structural analysis data analyzing unit 22. The structural analysis data analyzing unit 22 specifies phase information on the basis of the element information of the sample 100 acquired from the X-ray fluorescence analysis data, for example, through the use of a heavy atom multiple isomorphous replacement method and acquires an electron density of the single crystal of the sample 100 in addition to the measurement data of the diffraction pattern through the use of the data analysis. The single-crystal structure of the sample 100 is specified on the basis of the acquired electron density and the element information of the sample 100. The control and analysis unit 9 may be disposed in a single computer or may be distributed in plural computers.

The control and analysis unit 9 also controls the sample cooling unit 10. The control and analysis unit 9 maintains the sample 100 at a constant temperature by adjusting the temperature of the sprayed cooling nitrogen gas on the basis of temperature information from a temperature sensor disposed in the vicinity of the sample 100.

Figure 3:
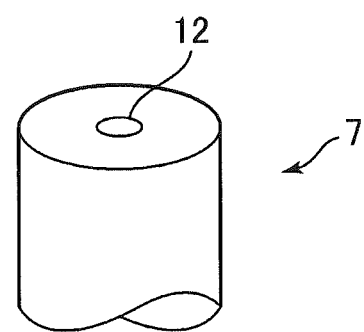
FIG. 3 is a diagram schematically illustrating the shape of a tip of an X-ray fluorescence detector of the X-ray multiple spectroscopic analyzer according to the first embodiment of the invention.

FIG. 3 is a diagram schematically illustrating the shape of a tip of the X-ray fluorescence detector 7 of the X-ray multiple spectroscopic analyzer 1 according to this embodiment. The X-ray fluorescence detector 7 has an outer diameter of 20 mm and has the light-receiving portion 12 at the tip thereof. Here, when the X-ray fluorescence detector 7 is an SDD, the light-receiving portion 12 is a circular plane having plural ring-like electrodes disposed thereon. When measuring the fluorescent X-rays of the sample 100, the X-ray fluorescence detector 7 is disposed in the X-ray multiple spectroscopic analyzer 1 so that the sensitivity for detecting the fluorescent X-rays radiated from the sample 100 may be the maximum. When the incidence direction of the fluorescent X-rays maximizing the light-receiving intensity of the fluorescent X-rays received by the light-receiving portion 12 is defined as the optical axis of the X-ray fluorescence detector 7, the optical axis of the X-ray fluorescence detector 7 preferably passes through the central part of the sample 100. The optical axis from the center of the light-receiving portion 12 is generally extended perpendicular to the light-receiving surface of the light-receiving portion 12 so as to increase the amount of the fluorescent X-rays received by the light-receiving portion 12, but is not limited to this example. The X-ray fluorescence detector 7 is preferably disposed so that the light-receiving portion 12 gets close to the sample 100 so as to raise the sensitivity for detecting the fluorescent X-rays radiated from the sample 100.

Figure 4:
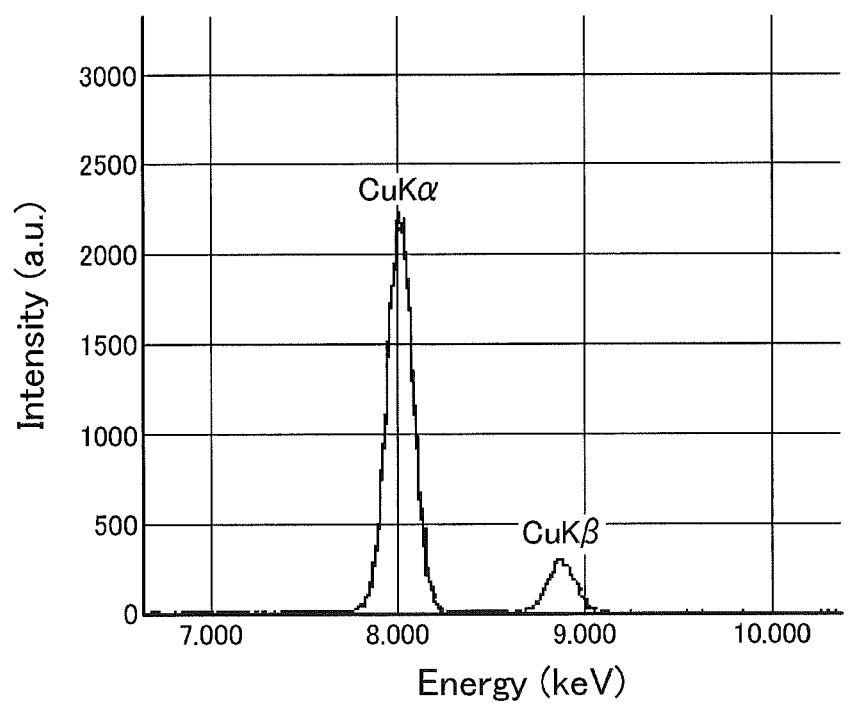
FIG. 4 is a diagram illustrating a spectrum of fluorescent X-rays detected by the X-ray fluorescence detector of the X-ray multiple spectroscopic analyzer according to the first embodiment of the invention.

FIG. 4 is a diagram illustrating a spectrum of the fluorescent X-rays detected by the X-ray fluorescence detector 7 of the X-ray multiple spectroscopic analyzer 1 according to this embodiment. The horizontal axis in the drawing represents the energy of the fluorescent X-rays and has a unit of keV. The vertical axis in the drawing represents the intensity of the X-rays and has a unit of detected count (a.u.). Here, the sample 100 is a single crystal of $C_{129}H_{149}Cu_4N_{11}O_{39}$ and the crystal size thereof is 0.1 mm×0.08 mm×0.06 mm. The measurement result of the fluorescent X-rays radiated from the sample 100 in a state where the distance between the light-receiving portion 12 of the X-ray fluorescence detector 7 and the sample 100 is set to 1 cm and the integration time is set to 100 seconds is shown in FIG. 4.

The content of Cu included in the sample 100 is 9.3% and the crystal size thereof is about 100 μm. The characteristic X-rays of Cu are observed from the spectrum of the fluorescent X-rays radiated from the single crystal having the content of Cu of 10% or less. When the fluorescent X-rays are measured at the same time in the period in which the diffracted X-rays are measured, it is seen that the signal intensity becomes lower by 20% because an X-ray shutter of the X-ray source 2 and the X-ray fluorescence detector 7 are not synchronized with each other, but the diffracted X-rays and the fluorescent X-rays can be measured at the same time. When the X-ray fluorescence detector 7 is synchronized with the X-ray shutter of the X-ray source 2, it is needless to say that more excellent spectrum of the fluorescent X-rays can be acquired. When the distance between the light-receiving portion 12 and the sample 100 is set to 2 cm, the characteristic X-rays of Cu sufficient to analyze the fluorescent X-rays are observed.

When analyzing the single-crystal structure, the X-ray diffraction analysis and the X-ray fluorescence analysis which are performed by different devices in the related art are performed by the X-ray multiple spectroscopic analyzer according to the invention. Accordingly, the increase in cost which is caused in the related art is suppressed. The labor of transferring the sample from a device to another device is saved and the X-ray diffraction measurement and the X-ray fluorescence measurement can be performed at the same time, thereby reducing the measuring time. Since two measurements can be performed under the same environment, it is possible to improve the accuracy of the measurement data, thereby improving the analysis capability. Particularly, when a sample having a large temporal variation and having poor stability is used, such an effect becomes more marked.

The time required for the X-ray diffraction measurement is generally longer than the time required for the X-ray fluorescence measurement. Accordingly, it is possible to reduce the measuring time by simultaneously performing the X-ray fluorescence measurement in the period in which the X-ray diffraction is measured. That is, in a first period which is a partial period of the period in which the X-ray diffraction detector 5 detects the diffracted X-rays generated from the sample 100, the X-ray fluorescence detector 7 detects the fluorescent X-rays radiated from the sample 100, whereby it is possible to reduce the measuring time.

After performing the X-ray fluorescence measurement and at the same time as performing the X-ray diffraction measurement, the X-ray fluorescence analyzing unit 24 can analyze the element information on the basis of the measurement data of the fluorescent X-rays stored in the X-ray fluorescence measurement data storage unit 23, the X-ray fluorescence analysis data storage unit 25 can store the X-ray fluorescence analysis data, and the X-ray fluorescence analysis data acquiring unit 26 can acquire and output the X-ray fluorescence analysis data to the structural analysis data analyzing unit 22. Accordingly, it is possible to greatly reduce the measuring time and the time required for the single-crystal structure analysis. In a second period which is a partial period of the period in which the X-ray diffraction detector 5 detects the diffracted X-rays generated from the sample 100 and which is a period subsequent to the first period, the X-ray fluorescence analyzing unit 24 analyzes the fluorescent X-rays on the basis of the measurement data of the fluorescent X-rays detected in the first period by the X-ray fluorescence detector 7, whereby the time required for the single-crystal structure analysis is greatly reduced.

The X-ray multiple spectroscopic analyzer according to the invention includes the X-ray fluorescence analysis data acquiring unit and quickly and easily uses the element information of the sample acquired through the X-ray fluorescence analysis for the single-crystal structure analysis, thereby further improving the analysis capability.

Through the X-ray fluorescence analysis, the element information (information of chemical composition) of the sample as a target can be acquired but the information of a crystal state of the sample cannot be acquired. Through the X-ray diffraction analysis, the information on whether the crystal state of the sample is good can be acquired, but the information on the chemical composition of the sample cannot be sufficiently acquired. Accordingly, since the X-ray diffraction measurement and the X-ray fluorescence measurement are separately performed in the past, it takes time to select a sample having a crystal state and a composition suitable for the measurement and the reliability thereof is lowered for a sample having a large temporal variation. On the contrary, by employing the X-ray multiple spectroscopic analyzer according to the invention, the information on the crystal state of a sample as a target can be acquired through the X-ray diffraction analysis and the information on the chemical composition of the sample can be acquired through the X-ray fluorescence analysis, whereby it is possible to reduce the measuring time, to reduce the cost, and to improve the reliability.

In the single-crystal structure analysis, since the measurement result of the X-ray diffraction measurement can be analyzed on the basis of the experimental chemical composition determined through the X-ray fluorescence analysis, it is possible to more accurately (more easily) determine the structure of a single crystal for a shorter time. For example, as difficulty in determining an initial phase in the single-crystal structure analysis, it is not clear whether a solvent used for the growth of a single crystal remains in the single-crystal sample as a target. The more accurate chemical composition than that of the sample is required for accurate calculation of normalized structure factors. The composition ratio of heavy elements and light elements can be acquired through the X-ray fluorescence analysis. When the presence of a solvent in the sample is expected from the composition ratio, it is possible to improve the success rate of phase determination in the initial step of the single-crystal structure analysis by adding the solvent molecule used for the growth of the single crystal to the chemical composition in advance when determining the single-crystal structure.

In structure analysis of protein having a new structure, a heavy atom isomorphous replacement method using a heavy atom substitute crystal is effective for the phase determination. However, the soaking using plural heavy atoms, the X-ray diffraction measurement, and the work of checking the presence of heavy atoms, and the like are required for searching for a heavy atom substitute crystal, which requires much labor and time. By employing the X-ray multiple spectroscopic analyzer according to the invention, the labor and time are greatly reduced, which is very effective for searching for a heavy atom substitute crystal.

For example, when the X-ray diffraction measurement and the X-ray fluorescence measurement are performed on a Pt substitute crystal in which potassium tetrachloroplatinate ($K_2PtCl_4$) as a heavy atom reagent is soaked in a chicken egg-white lysozyme crystal by the use of the X-ray multiple spectroscopic analyzer according to the invention, the presence of Pt could be confirmed in several minutes. Combinations of different $K_2PtCl_4$ concentrations and different soaking times are tested and, for example, the following four cases (Cases A to D) will be described below. The $K_2PtCl_4$ concentration and the soaking time in Case A are 2 mM and 130 minutes, the $K_2PtCl_4$ concentration and the soaking time in Case B are 2 mM and 63 hours, the $K_2PtCl_4$ concentration and the soaking time in Case C are 4 mM and 450 minutes, and the $K_2PtCl_4$ concentration and the soaking time in Case D are 10 mM and 10 minutes. When Pt substitute crystals are formed under these conditions and are measured and analyzed, the peak of a Pt spectrum is the highest in Case D and a heavy atom substitute crystal suitable for the phase determination is formed. In this way, by employing the X-ray multiple spectroscopic analyzer according to the invention, it is possible to greatly reduce the time required for preparing a heavy atom derivative.

By fixing the X-ray fluorescence detector 7, detecting the fluorescent X-rays radiated from the sample 100, and comparing the measured intensities of the X-rays, the position of the sample holder of the sample stage 4 supporting the sample 100 can be aligned. On the contrary, by fixing the sample 100 to the sample holder of the sample stage 4 and detecting the fluorescent X-rays through the use of the X-ray fluorescence detector 7, the position of the X-ray fluorescence detector 7 relative to the sample 100 can be aligned.

For example, by periodically measuring the fluorescent X-rays radiated from the sample 100 during the X-ray diffraction measurement and checking whether the spectrum of the measured fluorescent X-rays varies, it can be checked whether the sample 100 falls out of the sample holder or has misalignment relative to the sample holder, that is, the position of the sample 100 can be monitored, while rotation movement of the sample 100 by the rotation driving system(s) of the sample stage 4. Any of the measurement data of the fluorescent X-rays stored in the X-ray fluorescence measurement data storage unit 23 (or the analysis data of the fluorescent X-rays stored in the X-ray fluorescence analysis data storage unit 25) can be used as the result of the X-ray fluorescence analysis for each measurement for comparison. That is, the X-ray fluorescence detector 7 can be used to detect the state in which the sample stage 4 supports the sample 100 by detecting the fluorescent X-rays radiated from the sample.

From the viewpoint of symmetry, by changing the angle of only one side (for example, the upper side or the counterclockwise side in FIG. 1) of the optical axis of the X-rays emitted from the X-ray generating unit to the sample 100 when the X-ray diffraction detector 5 measures the X-ray diffraction, it is possible to acquire the whole diffraction pattern of the sample 100. Accordingly, when the sample stage 4 is sufficiently small, the X-ray fluorescence detector 7 can be disposed on the other side (the lower side or the clockwise side in FIG. 1) of the optical axis of the X-rays emitted from the X-ray generating unit. However, since the sample stage 4 includes the rotation driving system(s), it is actually often difficult to dispose the X-ray fluorescence detector 7 on the other side. Therefore, in consideration of the space necessary for the sample stage 4, the X-ray fluorescence detector 7 is disposed on the one side as shown in FIG. 1.

When a target metal used in the X-ray source 2 is Mo, the wavelength of the emitted X-rays is small and thus the movable space of the X-ray diffraction detector 5 necessary for the X-ray diffraction measurement may be small. That is, the angle to be counterclockwise rotated about the optical axis of the X-rays emitted from the X-ray generating unit shown in FIG. 1 is small and there is thus a margin for the space in which the X-ray fluorescence detector 7 should be disposed.

However, when the target metal used for the X-ray source 2 is Cu or Cr, the wavelength of the emitted X-rays is longer than that of Mo and the movable space of the X-ray diffraction detector 5 necessary for the X-ray diffraction measurement becomes larger, whereby the space in which the X-ray fluorescence detector 7 should be disposed is further limited. In this case, the space in which the X-ray fluorescence detector 7 should be disposed may overlap with the movable space of the X-ray diffraction detector 5. In order to cope with this case, the X-ray fluorescence detector 7 preferably includes a retreating mechanism. Here, the retreating mechanism is, for example, an XYZ stage and the control and analysis unit 9 controls the retreating mechanism to move the main body of the X-ray fluorescence detector 7. In the X-ray diffraction measurement, when the X-ray diffraction detector 5 gets farther from the space in which the main body of the X-ray fluorescence detector 7 should be disposed for the X-ray fluorescence measurement, for example, when it is located at the position shown in FIG. 1, the X-ray fluorescence detector 7 may be disposed at the position shown in FIG. 1 to perform the X-ray fluorescence measurement. Before the X-ray diffraction detector 5 gets close to the position of the X-ray fluorescence detector 7 shown in FIG. 1, the main body of the X-ray fluorescence detector 7 may be made to retreat to the outside of the movable space of the X-ray diffraction detector 5, that is, to the outside of the sample, through the use of the retreating mechanism.

The X-ray multiple spectroscopic analyzer 1 according to this embodiment includes the sample cooling unit 10 (not shown), and can perform the X-ray diffraction measurement even when the measuring time of the X-ray diffraction measurement is long and it is necessary to maintain the single crystal under the same temperature condition, for example, when the sample 100 is a single crystal of protein. As described above, since the sample cooling unit 10 is disposed above the sample 100, the space in which the X-ray fluorescence detector 7 should be disposed is further limited and thus the advantages of the invention become more marked. When it is necessary to maintain the single crystal under the same temperature condition, the X-ray diffraction measurement and the X-ray fluorescence measurement are performed under the same environment by the use of the same apparatus, whereby the advantages of the invention become more marked.

Second Embodiment

An X-ray multiple spectroscopic analyzer 1 according to a second embodiment of the invention has the same basic constitution as the X-ray multiple spectroscopic analyzer 1 according to the first embodiment. The X-ray multiple spectroscopic analyzer 1 according to this embodiment is different from the X-ray multiple spectroscopic analyzer 1 according to the first embodiment, in the shape of the X-ray fluorescence detector 7.

Figure 5:
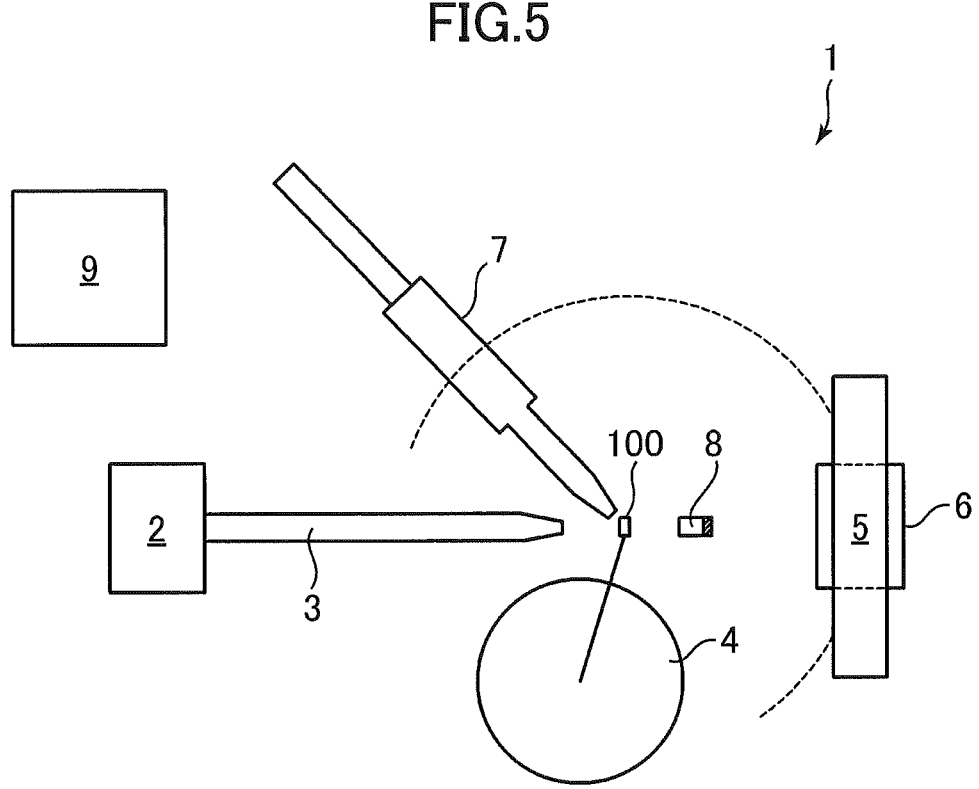
FIG. 5 is a diagram schematically illustrating the structure of an X-ray multiple spectroscopic analyzer according to a second embodiment of the invention.

FIG. 5 is a diagram schematically illustrating the structure of the X-ray multiple spectroscopic analyzer 1 according to this embodiment. As shown in the drawing, the shape of the tip of the X-ray fluorescence detector 7 is different from that of the X-ray fluorescence detector 7 shown in FIG. 1. The X-ray fluorescence detector 7 includes an X-ray blocking member 13 (not shown) as described later. When the light-receiving portion 12 of the X-ray fluorescence detector 7 is located at the position at which the fluorescent X-rays radiated from the sample 100 are detected, the X-ray blocking member 13 blocks the fluorescent X-rays radiated from the portion of the beam stopper 8 which is directly irradiated with the direct beam.

Figure 6:
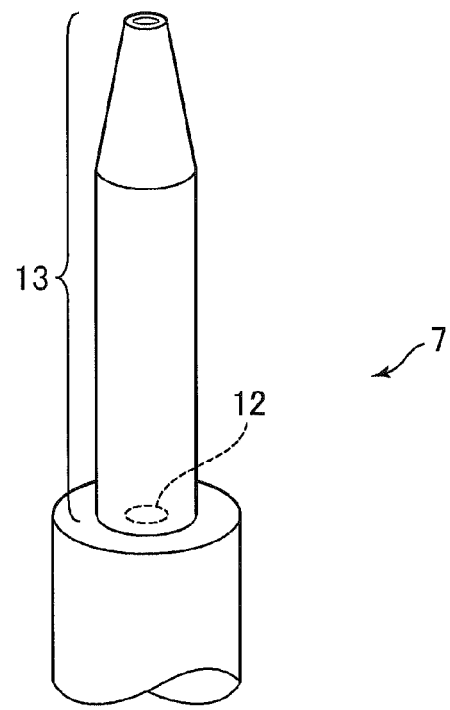
FIG. 6 is a diagram schematically illustrating the shape of a tip of an X-ray fluorescence detector of the X-ray multiple spectroscopic analyzer according to the second embodiment of the invention.

FIG. 6 is a diagram schematically illustrating the shape of the tip of the X-ray fluorescence detector 7 of the X-ray multiple spectroscopic analyzer 1 according to this embodiment. The X-ray fluorescence detector 7 further includes an X-ray blocking member 13 as shown in FIG. 6. Regarding the shape of the X-ray blocking member 13, a portion close to the main body of the X-ray fluorescence detector 7 has a hollow cylinder shape, a portion close to the tip thereof has a hollow circular truncated cone shape, and a circular opening is formed at the tip. That is, the X-ray blocking member 13 surrounds the peripheral edge of the light-receiving portion 12 of the X-ray fluorescence detector 7 with the hollow cylinder shape. The portion close to the tip of the X-ray blocking member 13 has a tapered shape and the radius of a section becomes slowly smaller toward the tip. The material of the X-ray blocking member 13 is not particularly limited as long as it can block the fluorescent X-rays from the beam stopper 8, and is stainless steel herein, but general metals may be used. Lead may be included if necessary.

Figure 7:
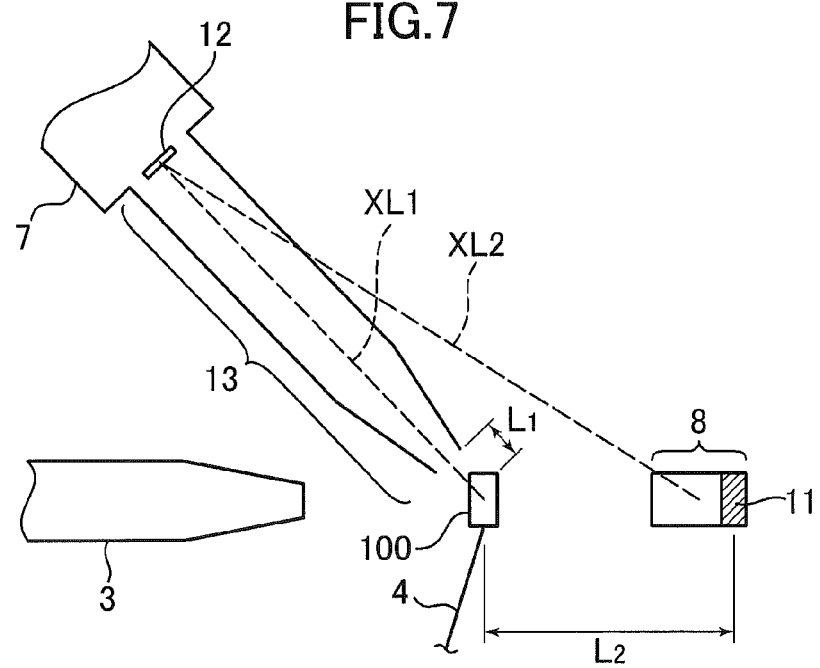
FIG. 7 is a diagram schematically illustrating arrangement of the X-ray fluorescence detector of the X-ray multiple spectroscopic analyzer according to the second embodiment of the invention.

FIG. 7 is a diagram schematically illustrating the arrangement of the X-ray fluorescence detector 7 of the X-ray multiple spectroscopic analyzer 1 according to this embodiment. The outer diameter of the main body of the X-ray fluorescence detector 7 is 20 mm, the outer diameter of the hollow cylinder portion of the X-ray blocking member 13 is 12 mm, and the distance from the light-receiving portion 12 to the tip of the X-ray blocking member 13 is 20 mm. The distance L1 from the tip of the X-ray blocking member 13 to the sample 100 is 2 mm.

The sample 100 and the beam stopper 8 are sequentially arranged in the optical axis of the X-rays incident on the sample 100 from the collimator of the optical system 3. The outer diameter of the collimator is 13 mm. As shown in FIG. 7, a core 11 formed of lead is disposed at the position of the beam stopper 8 which is irradiated with the direct beam of X-rays, and the core 11 is supported by a holder. That is, the core 11 is a portion of the beam stopper 8 which is directly irradiated with the direct beam of X-rays. By absorbing the direct beam of X-rays incident on the sample 100 by the use of the lead of the core 11, the core 11 of the beam stopper 8 blocks the direct beam of X-rays. The distance L2 between the sample 100 and the core 11 of the beam stopper 8 is 11 mm. Here, the beam stopper 8 includes the core 11 formed of lead, but the beam stopper 8 is not limited to this constitution and may be, for example, of an integrated type formed of lead alloy. In this case, the X-ray blocking member 13 according to the invention blocks the fluorescent X-rays radiated from the portion of the integrated type beam stopper which is directly irradiated with the direct beam of X-rays.

The X-ray fluorescence detector 7 shown in FIG. 7 is disposed at a position suitable for detecting the fluorescent X-rays radiated from the sample 100. It is preferable that the optical axis of the X-ray fluorescence detector 7 passes through the center of the area where the sample 100 is irradiated with the direct beam of X-rays. Since the optical axis of the X-ray fluorescence detector 7 extends perpendicularly to the plane of the light-receiving portion 12 from the center of light-receiving portion 12, the central portion of the fluorescent X-rays XL1 radiated to the light-receiving portion 12 from the sample 100 reaches the center of the light-receiving portion 12. In the drawing, the central portion of the fluorescent X-rays XL1 radiated to the light-receiving portion 12 from the sample 100 is indicated by a broken line.

On the contrary, a part of the X-ray blocking member 13 is disposed between the light-receiving portion 12 and the beam stopper 8 and the X-ray blocking member 13 blocks the fluorescent X-rays radiated to the light-receiving portion 12 from the beam stopper 8. Particularly, the X-ray blocking member 13 blocks the fluorescent X-rays XL2 radiated to the light-receiving portion 12 from the core 11. In the drawing, the central portion of the fluorescent X-rays XL2 radiated to the light-receiving portion 12 from the core 11 is indicated by a broken line. If the X-ray blocking member 13 is not present, the fluorescent X-rays radiated to the light-receiving portion 12 from the beam stopper 8 reaches the light-receiving portion 12. However, since the X-ray blocking member 13 is present, the fluorescent X-rays radiated to the light-receiving portion 12 from the beam stopper 8, particularly, the fluorescent X-rays XL2 radiated to the light-receiving portion 12 from the core 11, are blocked by the X-ray blocking member 13.

In general, in order to prevent the direct beam of X-rays from reaching the X-ray diffraction detector and damaging the X-ray diffraction detector and in order to reduce noise due to the scattered X-rays generated by the direct beam of X-rays reaching the structures of the apparatus, or for the purpose of safety measure for a worker, the beam stopper is disposed in the X-ray spectroscopic analyzer. The portion of the beam stopper blocking the direct beam of X-rays is formed of heavy metal such as lead and the fluorescent X-rays are radiated from the heavy metal such as lead forming the portion of the beam stopper in response to the direct beam of X-rays reaching the beam stopper when a sample is irradiated with the direct beam of X-rays. Here, lead is used as an example of the representative material of the portion of the beam stopper.

The X-ray fluorescence detector such as an X-ray detector for EDX measures the fluorescent X-rays radiated from the lead of the beam stopper located in the vicinity at the same time as measuring the fluorescent X-rays radiated from the sample. The fluorescent X-rays from the lead of the beam stopper are information disturbing the X-ray fluorescence analysis of a sample. When the fluorescent X-rays radiated from the lead of the beam stopper are measured, it is difficult to determine whether the spectrum of the lead included in the measured fluorescent X-rays is based on the lead included in the sample or the lead included in the beam stopper. When the lead remains in the sample, the intensity in the quantitative analysis of the lead is inaccurately measured, thereby making the X-ray fluorescence analysis difficult. An element having a characteristic X-ray of a wavelength close to the wavelength of the characteristic X-ray of lead is present like platinum. Accordingly, as in the example shown in FIG. 8 to be described later, when platinum is included in a sample, the spectrum of platinum and the spectrum of lead partially overlap with the spectrum of the measured fluorescent X-rays, thereby making the X-ray fluorescence analysis difficult.

In order to suppress the detection of the fluorescent X-rays radiated from the beam stopper, the X-ray fluorescence detector has only to be disposed as parallel as possible to the beam stopper. However, since the X-ray diffraction detector is disposed in the vicinity of the beam stopper and the X-ray diffraction detector moves in angle relative to the sample so as to take a diffraction pattern in a wide diffraction angle range, the X-ray fluorescence detector disposed in the vicinity of the beam stopper serves as an obstacle of the X-ray diffraction measurement. When a device changing the environment of a sample is provided, it is difficult to dispose the X-ray fluorescence detector in the vicinity of the beam stopper.

In consideration of the movable space of the X-ray diffraction detector necessary for the X-ray diffraction measurement, the X-ray fluorescence detector is preferably disposed in the vicinity of the X-ray generating unit, but the angle formed by the viewing direction from the X-ray fluorescence detector to the sample and the viewing direction from the X-ray fluorescence detector to the beam stopper becomes smaller and it is difficult to suppress the detection of the fluorescent X-rays radiated from the beam stopper.

The X-ray fluorescence detector 7 according to this embodiment includes the X-ray blocking member 13 so as to solve this problem. In the X-ray multiple spectroscopic analyzer performing both the X-ray diffraction analysis and the X-ray fluorescence analysis, it is possible to detect the fluorescent X-rays radiated from the sample while suppressing the influence of the fluorescent X-rays radiated from the beam stopper, by employing the X-ray fluorescence detector 7 according to this embodiment. The advantages of the X-ray multiple spectroscopic analyzer 1 according to this embodiment will be described below.

Figure 8:
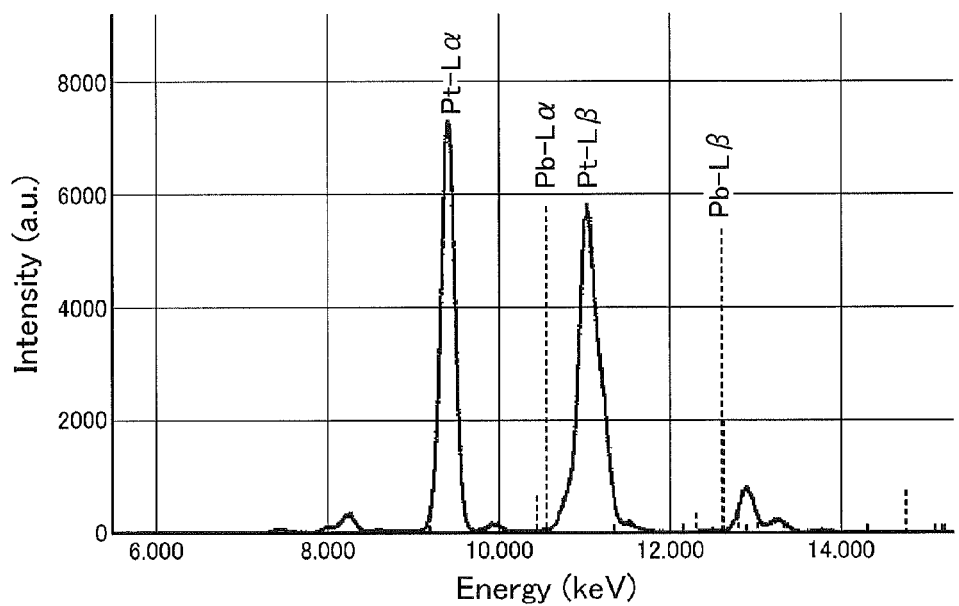
FIG. 8 is a diagram illustrating a spectrum of fluorescent X-rays detected by the X-ray fluorescence detector of the X-ray multiple spectroscopic analyzer according to the second embodiment of the invention.

FIG. 8 is a diagram illustrating a spectrum of fluorescent X-rays detected by the X-ray fluorescence detector 7 of the X-ray multiple spectroscopic analyzer 1 according to this embodiment. The horizontal axis and the vertical axis in the drawing are the same as those in FIG. 4, but the scales of the horizontal axis and the vertical axis are different from those in FIG. 4. Here, the measurement result of the fluorescent X-rays of a sample 100 with an integration time of 25 seconds when the sample 100 is a single crystal of $K_2PtCl_4$ and the X-ray fluorescence detector 7 is disposed at the position shown in FIG. 7 is shown in FIG. 8.

In FIG. 8, high peaks with an X-ray intensity greater than 5000 are observed both in the energy value of an $L\alpha$ ray of Pt (platinum) and in the energy value of an $L\beta$ ray of Pt, and the fluorescent X-rays of Pt included in the sample 100 are detected. On the contrary, no peak with an X-ray intensity greater than the background intensity of X-rays is observed either in the energy value of the $L\alpha$ ray of Pb (Lead) or the energy value of the $L\beta$ ray of Pb which are indicated by a broken line in the drawing.

Figure 9:
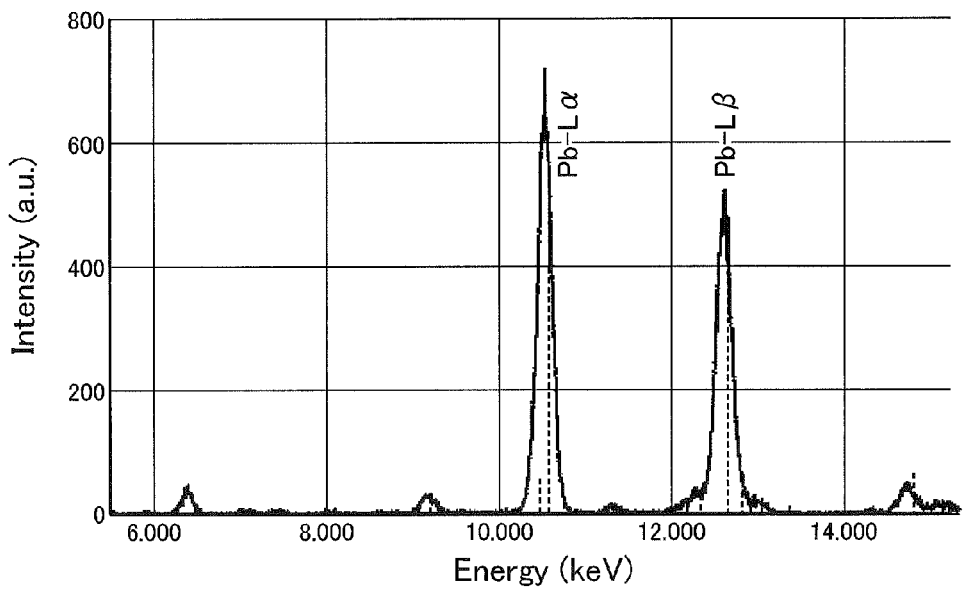
FIG. 9 is a diagram illustrating a spectrum of fluorescent X-rays from a beam stopper, which is detected by the X-ray fluorescence detector of the X-ray multiple spectroscopic analyzer according to the first embodiment of the invention.

FIG. 9 is a diagram illustrating a spectrum of fluorescent X-rays from the beam stopper 8, which is detected by the X-ray fluorescence detector 7 of the X-ray multiple spectroscopic analyzer 1 according to the first embodiment. The horizontal axis and the vertical axis in the drawing are the same as those in FIG. 8, but the scale of the vertical axis is different from that in FIG. 8. The X-ray fluorescence detector 7 according to the first embodiment does not include the X-ray blocking member 13, unlike the X-ray fluorescence detector 7 according to this embodiment. In order to measure the intensity of the fluorescent X-rays radiated from the beam stopper 8, a sample 100 is not mounted on the sample stage 4 herein. The measurement result of the fluorescent X-rays with an integration time of 300 seconds is shown in FIG. 9. Here, since the sample 100 is not mounted on the sample stage 4, it is considered that the spectrum of fluorescent X-rays is detected by mainly the fluorescent X-rays radiated from the lead of the core 11 of the beam stopper 8.

In FIG. 9, peaks with an X-ray intensity greater than 500 are observed both in the energy value of an $L\alpha$ ray of Pb and in the energy value of an $L\beta$ ray of Pb and the fluorescent X-rays radiated from the lead of the beam stopper 8 are detected. When the fluorescent X-rays of the sample 100 are measured by the use of the X-ray multiple spectroscopic analyzer 1 according to the first embodiment, the peak of the characteristic X-ray of Pb shown in FIG. 9 is also observed. On the contrary, as shown in FIG. 8, in the X-ray multiple spectroscopic analyzer 1 according to this embodiment, it is thought that the fluorescent X-rays radiated to the light-receiving portion 12 from the beam stopper 8 are satisfactorily blocked by the X-ray blocking member 13.

Figure 10A:
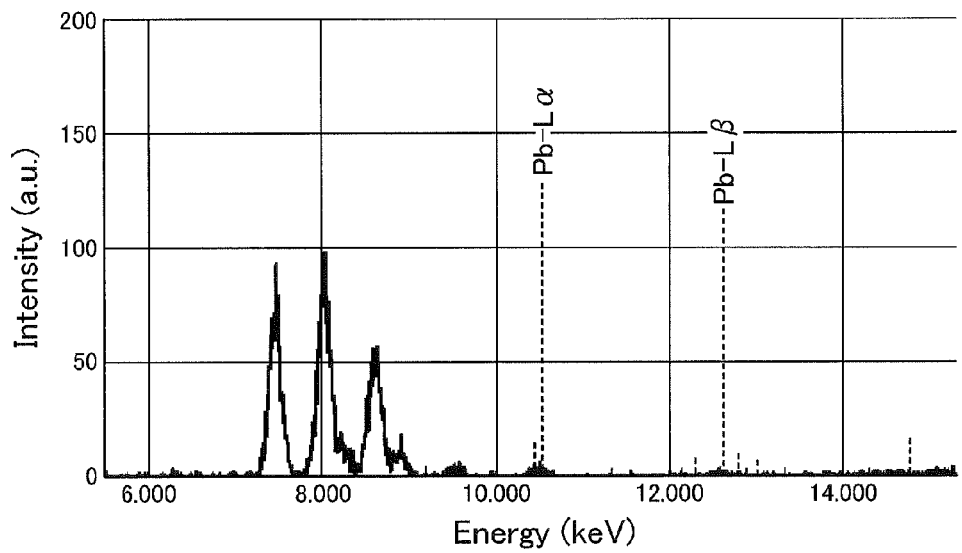
FIG. 10A is a diagram illustrating a spectrum of fluorescent X-rays from a beam stopper, which is detected by the X-ray fluorescence detector of the X-ray multiple spectroscopic analyzer according to the second embodiment of the invention.

FIG. 10A is a diagram illustrating a spectrum of fluorescent X-rays from the beam stopper 8, which is detected by the X-ray fluorescence detector 7 of the X-ray multiple spectroscopic analyzer 1 according to this embodiment. The horizontal axis and the vertical axis in the drawing are the same as those in FIG. 8, but the scale of the vertical axis is different from that in FIG. 8. The spectrum of fluorescent X-rays shown in FIG. 10A is obtained through the same measurement as the measurement of the fluorescent X-rays shown in FIG. 9. That is, the measurement result of the fluorescent X-rays radiated from the beam stopper 8 with an integration time of 300 seconds without mounting the sample 100 on the sample stage 4 is shown in FIG. 10A. In FIG. 10A, any visible peak, which is observed in the spectrum of fluorescent X-rays shown in FIG. 9, is not observed in the energy value of $L\alpha$ rays and the energy value of $L\beta$ rays of Pb.

Figure 10B:
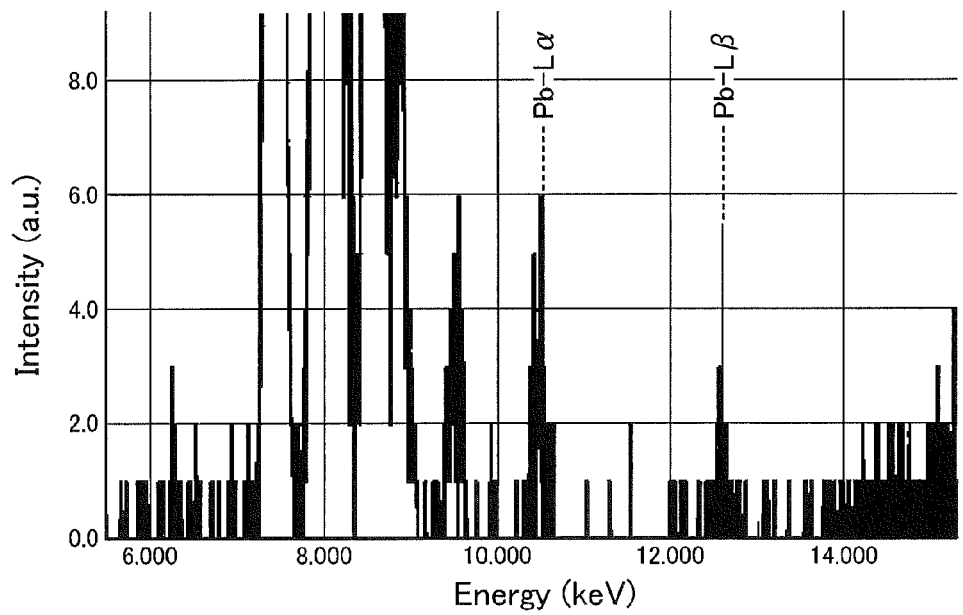
FIG. 10B is an enlarged diagram of FIG. 10A in the vertical axis direction.

FIG. 10B is an enlarged diagram of FIG. 10A in the vertical axis direction. That is, the scale of the horizontal axis of FIG. 10B is the same as in FIG. 10A, but the scale of the vertical axis of FIG. 10B is smaller than that of FIG. 10A. As shown in FIG. 10B, the X-ray intensity appearing in the energy value of Lα rays of Pb is about 6, and the detected fluorescent X-rays radiated from the core 11 of the beam stopper 8 is reduced to 1/100 by the X-ray blocking member 13.

As described above, heavy atoms such as Pt (platinum) are often used in the heavy atom multiple isomorphous replacement method. The wavelength of the characteristic X-rays of Pt is close to the wavelength of the characteristic X-rays of the heavy atoms such as Pb (lead) as described above, and it is made to be difficult to analyze the fluorescent X-rays due to the fluorescent X-rays radiated from the beam stopper when Pt is included in the sample 100 or when the X-ray fluorescence analysis is performed on a heavy atom substitute crystal (heavy atom derivative) formed by soaking a single-crystal sample in a solution including Pt through the use of the heavy atom multiple isomorphous replacement method. Accordingly, in the X-ray multiple spectroscopic analyzer 1 according to this embodiment, it is possible to suppress the detection of the fluorescent X-rays radiated from the beam stopper 8, thereby markedly exhibiting the advantages of the invention.

Figure 11:
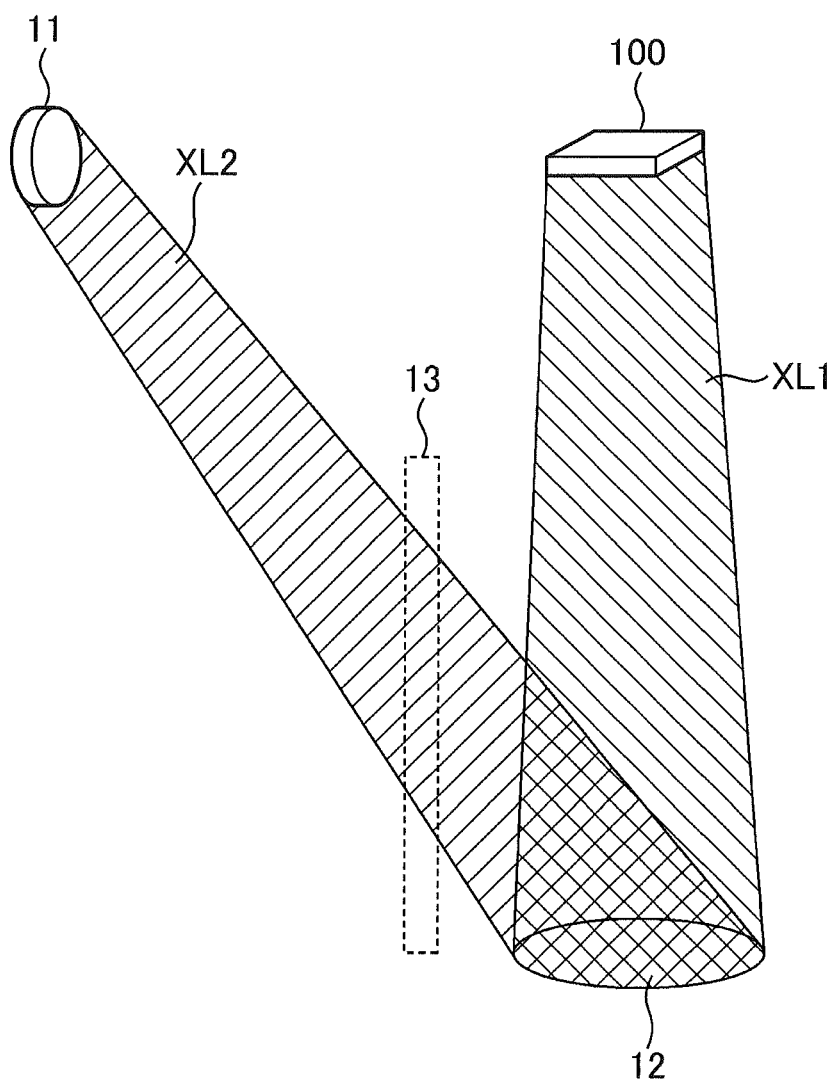
FIG. 11 is a diagram schematically illustrating the function of an X-ray blocking member according to the second embodiment of the invention.

FIG. 11 is a diagram schematically illustrating the function of the X-ray blocking member 13 according to this embodiment. The X-ray blocking member 13 blocks the fluorescent X-rays radiated to the light-receiving portion 12 from the beam stopper 8.

The fluorescent X-rays received by the light-receiving portion 12 enter the inside of the X-ray fluorescence detector 7 through the light-receiving portion 12 and are converted into electrical signals. When it is assumed that the entire area of the sample 100 is irradiated with the direct beam of X-rays emitted from the X-ray generating unit, fluorescent X-rays are radiated in all directions from the sample 100 irradiated with the X-rays. The fluorescent X-rays XL1 radiated to the light-receiving portion 12 from the sample 100 out of the fluorescent X-rays radiated from the sample 100 are shown in FIG. 11. The fluorescent X-rays XL1 radiated to the light-receiving portion 12 from the sample 100 shown in the drawing are present in a space formed by connecting the sample 100 and the light-receiving portion 12, that is, a space formed by connecting any point of the inside (and the surface) of the sample 100 and any point of the light-receiving portion 12. Similarly, the beam stopper 8 is also irradiated with the direct beam of X-rays emitted from the X-ray generating unit and the fluorescent X-rays are radiated in all directions from the beam stopper 8. Particularly, the core 11 is a portion of the beam stopper 8 which is directly irradiated with the direct beam of X-rays and strong fluorescent X-rays are radiated from the core 11. The fluorescent X-rays XL2 radiated to the light-receiving portion 12 from the core 11 out of the fluorescent X-rays radiated from the beam stopper 8 are shown in FIG. 11. The fluorescent X-rays XL2 radiated to the light-receiving portion 12 from the core 11 shown in the drawing are similarly present in a space formed by connecting any point of the inside (and the surface) of the core 11 and any point of the light-receiving portion 12.

The X-ray blocking member 13 blocks at least a part of the fluorescent X-rays radiated to the light-receiving portion 12 from the beam stopper 8, whereby the detection of the fluorescent X-rays radiated from the beam stopper 8 by the X-ray fluorescence detector 7 is suppressed. It is more preferable that all the fluorescent X-rays XL2 radiated to the light-receiving portion 12 from the core 11 be blocked by the X-ray blocking member 13. Accordingly, it is possible to further prevent the X-ray fluorescence detector 7 from detecting the fluorescent X-rays radiated from the beam stopper 8. In this case, the X-ray blocking member 13 divides the space formed by connecting the core 11 and the light-receiving portion 12 and blocks all the fluorescent X-rays XL2 radiated to the light-receiving portion 12 from the core 11 shown in FIG. 11. The X-ray blocking member 13 more preferably divides the space formed by connecting the beam stopper 8 and the light-receiving portion 12.

Figure 12:
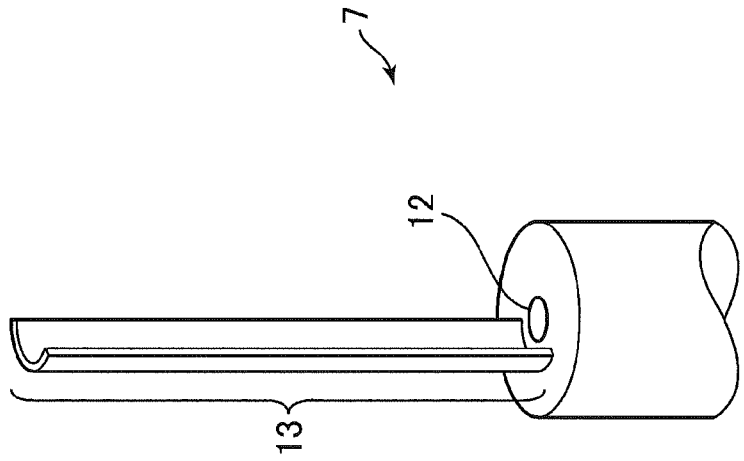
FIG. 12 is a diagram schematically illustrating another example of the shape of the tip of the X-ray fluorescence detector of the X-ray multiple spectroscopic analyzer according to the second embodiment of the invention.

FIG. 12 is a diagram schematically illustrating another example of the shape of the tip of the X-ray fluorescence detector 7 of the X-ray multiple spectroscopic analyzer 1 according to this embodiment. Unlike FIG. 6, the X-ray blocking member 13 surrounds only a part of the peripheral edge of the light-receiving portion 12. However, with this structure surrounding only a part of the peripheral edge, as shown in FIG. 11, the fluorescent X-rays radiated to the light-receiving portion 12 from the beam stopper, particularly, the fluorescent X-rays XL2 radiated to the light-receiving portion 12 from the core 11, can be blocked by disposing the X-ray blocking member 13 between the light-receiving portion 12 and the beam stopper 8.

Figure 13:
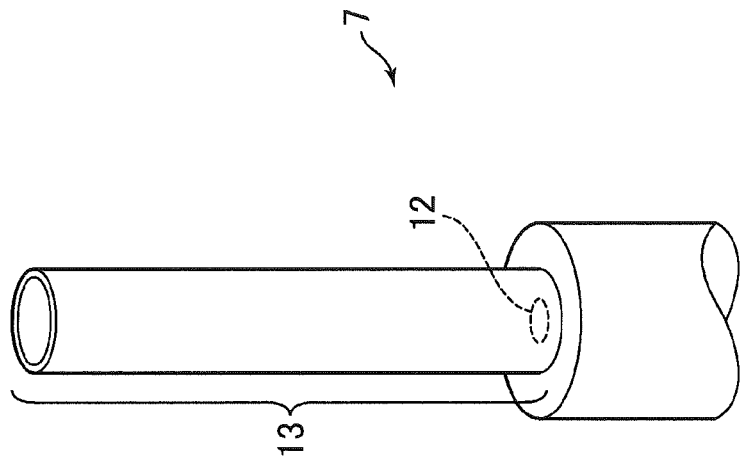
FIG. 13 is a diagram schematically illustrating still another example of the shape of the tip of the X-ray fluorescence detector of the X-ray multiple spectroscopic analyzer according to the second embodiment of the invention.

FIG. 13 is a diagram schematically illustrating still another example of the shape of the tip of the X-ray fluorescence detector 7 of the X-ray multiple spectroscopic analyzer 1 according to this embodiment. Similarly to FIG. 6 and unlike FIG. 12, the X-ray blocking member 13 has a structure surrounding all the peripheral edge of the light-receiving portion 12 and has a hollow cylinder shape. Since the peripheral edge of the light-receiving portion 12 is surrounded, the X-ray blocking member 13 can block the X-rays received by the light-receiving portion 12 from the other directions as well as the fluorescent X-rays radiated to the light-receiving portion 12 from the beam stopper 8 and it is thus possible to more easily adjust the arrangement of the X-ray fluorescence detector 7.

Figure 14:
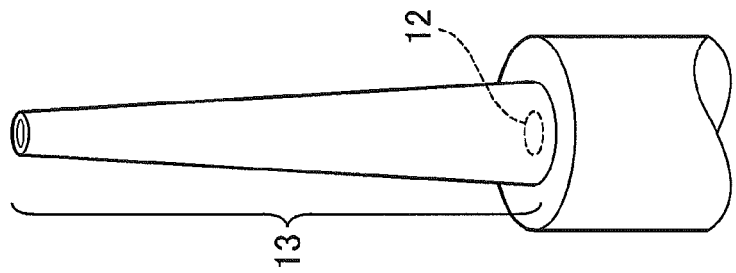
FIG. 14 is a diagram schematically illustrating still another example of the shape of the tip of the X-ray fluorescence detector of the X-ray multiple spectroscopic analyzer according to the second embodiment of the invention.

FIG. 14 is a diagram schematically illustrating still another example of the shape of the tip of the X-ray fluorescence detector 7 of the X-ray multiple spectroscopic analyzer 1 according to this embodiment. Since the X-ray blocking member 13 has a circular truncated cone shape and has a structure surrounding the whole peripheral edge of the light-receiving portion 12, and the X-ray blocking member 13 has a tapered shape.

An opening is formed at the tip of the X-ray blocking member 13 shown in FIGS. 6 and 14, and the amount of X-rays reaching the light-receiving portion 12 out of the fluorescent X-rays XL1 radiated to the light-receiving portion 12 from the sample 100 can be controlled depending on the shape of the opening, particularly, the magnitude of the opening radius. By increasing the opening radius of the opening, a larger amount of X-rays out of the fluorescent X-rays XL1 can reach the light-receiving portion 12, but as the opening radius of the opening increases, more X-rays from the other directions reach the light-receiving portion 12. On the contrary, by reducing the opening radius of the opening, the amount of X-rays reaching the light-receiving portion 12 out of the fluorescent X-rays XL1 can be more limited, but the X-rays from the other directions can be further prevented from reaching the light-receiving portion 12. The shape of the opening including the opening radius can be preferably selected in consideration of the intensity of the fluorescent X-rays radiated from the sample 100 and the intensity of the fluorescent X-rays from the other directions.

As described in the first embodiment, in the X-ray multiple spectroscopic analyzer 1 according to this embodiment, the position of the sample stage 4 or the position of the X-ray fluorescence detector 7 can be aligned by causing the X-ray fluorescence detector 7 to detect the fluorescent X-rays radiated from the sample 100. By employing the X-ray blocking member 13 which is shown in FIG. 6 or 14 and of which the tip has a tapered shape, the directivity of the fluorescent X-rays detected by the X-ray fluorescence detector 7 increases, thereby more accurately performing the alignment. By employing an X-ray blocking member 13 having a small opening radius, it is possible to achieve alignment with higher precision.

As described in the first embodiment, in the X-ray multiple spectroscopic analyzer 1 according to this embodiment, the position of the sample 100 can be monitored by causing the X-ray fluorescence detector 7 to detect the fluorescent X-rays radiated from the sample 100. By employing the X-ray blocking member 13 which is shown in FIG. 6 or 14 and of which the tip has a tapered shape, the directivity of the fluorescent X-rays detected by the X-ray fluorescence detector 7 increases, thereby more accurately monitoring the position of the sample 100.

Figure 15:
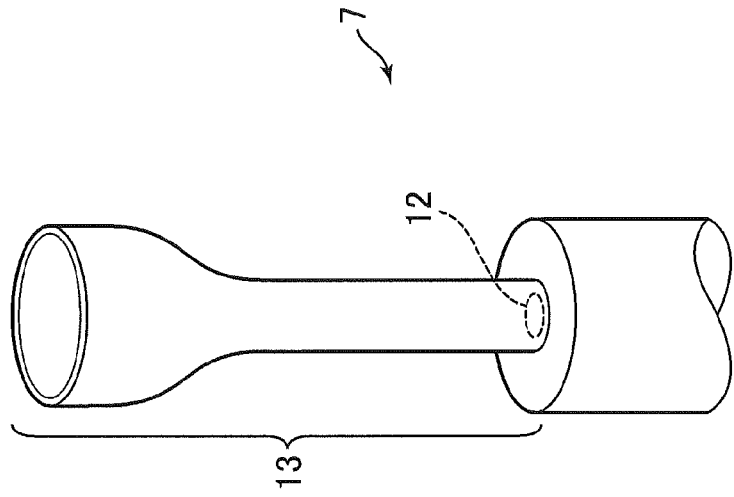
FIG. 15 is a diagram schematically illustrating still another example of the shape of the tip of the X-ray fluorescence detector of the X-ray multiple spectroscopic analyzer according to the second embodiment of the invention.

FIG. 15 is a diagram schematically illustrating still another example of the shape of the tip of the X-ray fluorescence detector 7 of the X-ray multiple spectroscopic analyzer 1 according to this embodiment. Unlike FIGS. 6 and 14, the tip of the X-ray blocking member 13 shown in FIG. 15 has an inverted tapered shape. Plural hollow light-guiding tubes (capillaries) are disposed in the X-ray blocking member 13. The hollow light-guiding tubes have a characteristic of passing the X-rays incident from the extending direction of the tubes and the X-ray blocking member 13 serves as a polycapillary guiding the X-rays passing through the inside of the opening to the light-receiving portion 12. Accordingly, by employing the X-ray blocking member 13 shown in FIG. 15, it is possible to detect more fluorescent X-rays radiated from the sample 100 while suppressing the detection of the fluorescent X-rays radiated from the beam stopper 8, thereby improving the detection sensitivity.

The shape of the X-ray blocking member 13 has been described hitherto. The X-ray blocking member 13 having the optimal shape can be used depending on the intensity of the fluorescent X-rays radiated from the sample 100 or the desired detection precision.

According to the invention, the X-ray multiple spectroscopic analyzer 1 can simultaneously perform both the X-ray diffraction measurement and the X-ray fluorescence measurement. As described above, the X-ray diffraction detector 5 angularly moves about the sample 100 by the use of the rotation driving system 6 when measuring the X-ray diffraction. Accordingly, the X-ray fluorescence detector 7 is preferably disposed closer to the X-ray generating unit about the sample 100 so as not to disturb the measurement of the X-ray diffraction. Here, in consideration of a plane perpendicular to the optical axis of the X-rays emitted from the X-ray generating unit and passing through any of the sample 100, the light-receiving portion 12 of the X-ray fluorescence detector 7 has only to be disposed closer to the X-ray generating unit with respect to the plane. For example, as shown in FIG. 7, the light-receiving portion 12 of the X-ray fluorescence detector 7 has only to be disposed on the left side of the sample 100 supported by the sample stage 4. In consideration of the direction of the diffracted X-rays counterclockwise from the sample 100, as it goes ahead in the direction toward the X-ray generating unit (in the emission direction of the direct beam of X-rays), the intensity of the diffracted X-rays passing through the sample 100 is lowered. Therefore, it is preferable that the X-ray fluorescence detector 7 be disposed as parallel as possible to the optical system 3 of the X-ray generating unit. The same is true of the X-ray multiple spectroscopic analyzer 1 according to the first embodiment.

In order to improve the detection sensitivity of the fluorescent X-rays radiated from the sample 100, the light-receiving portion 12 of the X-ray fluorescence detector 7 is preferably disposed as close as possible to the sample 100. However, due to the sectional size of the main body of the X-ray fluorescence detector 7, the distance by which the X-ray fluorescence detector 7 can get close to the sample 100 is limited from the relationship with other devices. For example, the section of the main body of the X-ray fluorescence detector 7 shown in FIG. 7 has a circular shape and the outer diameter thereof is 20 mm. However, even when the sectional size of the main body of the X-ray fluorescence detector 7 is great and the light-receiving portion 12 of the X-ray fluorescence detector 7 is located at the limit position at which it can approach the sample 100, the X-ray fluorescence detector 7 according to the second embodiment includes the X-ray blocking member 13 and the tip of the X-ray blocking member 13 can be set to be close to the sample 100, thereby blocking the fluorescent X-rays radiated to the light-receiving portion 12 from the beam stopper 8. In this case, it is preferable that the section of the X-ray blocking member 13 be located inside the outer edge of the section of the main body of the X-ray fluorescence detector 7. For example, the outer diameter of the hollow cylinder portion of the X-ray blocking member 13 shown in FIGS. 6 and 7 is set to 12 mm. As shown in FIG. 7, by setting the tip of the X-ray blocking member 13 to a tapered shape, the distance L1 from the tip of the X-ray blocking member 13 to the sample 100 is set to 2 mm and the tip of the X-ray blocking member 13 extends closer to the sample 100 while avoiding interference with other devices, for example, the optical system 3 of the X-ray generating unit. The X-ray blocking member 13 shown in FIG. 12 surrounds only a part of the peripheral edge of the light-receiving portion 12 and does not extend to the opposite side of the fluorescent X-rays radiated to the light-receiving portion 12 from the beam stopper 8, whereby the interference with other devices, for example, the optical system 3 of the X-ray generating unit is suppressed.

The X-ray multiple spectroscopic analyzers 1 according to the first and second embodiments of the invention are described hitherto. Although it has been stated that the X-ray multiple spectroscopic analyzer according to the invention is used as an X-ray spectroscopic analyzer performing single-crystal structure analysis, the technique on the X-ray blocking member 13 of the X-ray fluorescence detector 7 according to the second embodiment is not limited to the X-ray multiple spectroscopic analyzer, but may be applied to any structure as long as it is an X-ray multiple spectroscopic analyzer including an X-ray diffraction detector, an X-ray fluorescence detector, and a beam stopper. For example, the technique can be applied to a transmissive X-ray multiple spectroscopic analyzer which can perform X-ray diffraction analysis and X-ray fluorescence analysis of a powder-like sample including micro crystals. When the X-ray blocking member blocks the fluorescent X-rays based on the X-rays from the X-ray source other than the beam stopper, the relevant technique can be employed.

Third Embodiment

In a third embodiment of the invention, the invention is applied to single-crystal structure analysis when a predetermined atom included in a compound constituting a sample has a possibility of plural kind of atoms. The structure of an X-ray multiple spectroscopic analyzer 1 according to this embodiment is the same as the structure of the X-ray multiple spectroscopic analyzer 1 according to the first or second embodiment. When a predetermined atom included in a compound constituting a sample has a possibility of plural kind of atoms, the advantages of the invention become marked.

For example, when a compound constituting a sample is a metal complex compound, the central metal of the metal complex compound may be one of plural kind of metals. The crystal structures of meal complex compounds have a lot of common points and it is difficult to specify the atomic species of the central metal through the X-ray diffraction analysis with predetermined precision. When the X-rays are scattered by electrons and the difference in the number of electrons among plural possible metal atoms is small, it is more difficult to specify the atomic species. In order to specify an atomic species through the X-ray diffraction measurement, the measurement and analysis with higher precision are necessary. For example, when plural possible metal atoms are nickel (Ni) or zinc (Zn), it is difficult to specify the atomic species and the measurement and analysis with very high precision are necessary for specifying the atomic species. Accordingly, a lot of labor and time are required for determining the structure through the single-crystal structure analysis.

Figure 16B:
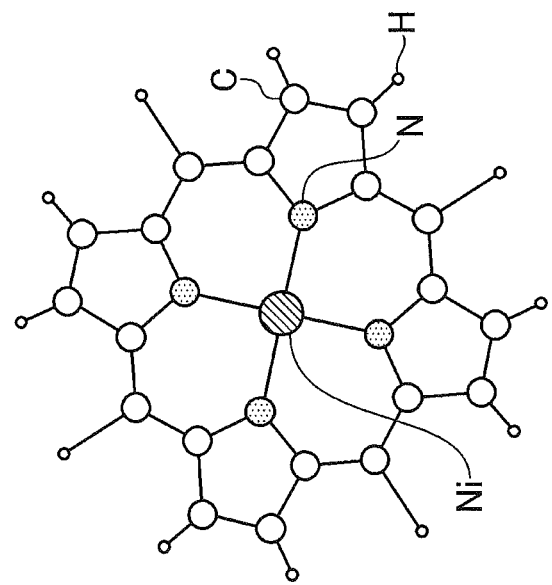
FIGS. 16A and 16B are diagrams illustrating an example of the structure of a molecule model of a compound which is subjected to single-crystal structure analysis according to a third embodiment of the invention.
Figure 16A:
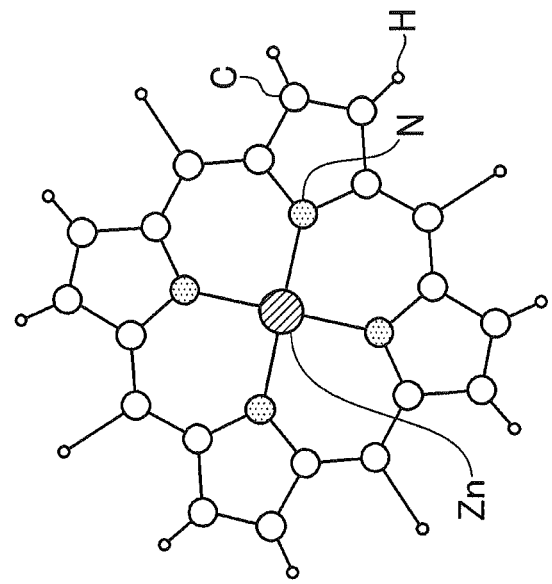

FIGS. 16A and 16B are diagrams illustrating examples of the structure of a molecular model of a compound to be subjected to the single-crystal structure analysis according to this embodiment. The metal complex compound shown in FIG. 16A is porphyrin having Ni as a central metal and the metal complex compound shown in FIG. 16B is porphyrin having Zn as a central metal. Four nitrogens (N) are bonded to the central metal (Ni or Zn) and plural carbons (C) and hydrogens (H) are bonded thereto, as shown in the drawings. Even when a sample includes several metal complex compounds, the species of the central metals of the metal complex compounds can be determined by acquiring the information on the chemical composition of the sample through the X-ray fluorescence analysis.

Even through the X-ray diffraction measurement with lower precision, it is possible to determine the crystal structure by using the result of the X-ray fluorescence analysis in the single-crystal structure analysis. By employing the X-ray multiple spectroscopic analyzer 1 according to the invention, the X-ray diffraction measurement and the X-ray fluorescence measurement can be performed in parallel, the X-ray fluorescence analyzing unit 24 of the control and analysis unit 9 can perform the X-ray fluorescence analysis, the structural analysis data analyzing unit 22 can determine an atomic species from the X-ray fluorescence analysis data output from the X-ray fluorescence analyzing unit 24, and the single-crystal structure analysis can be performed on the basis of the determined atomic species, thereby determining the crystal structure of the sample. Therefore, it is possible to achieve a reduction in time, a decrease in cost, and an improvement in reliability. Particularly, when the wavelength of the characteristic X-ray of the central metal is close to the wavelength of the characteristic X-ray of Pb, the advantages of the invention can be better exhibited by using the X-ray multiple spectroscopic analyzer 1 according to the second embodiment.

Fourth Embodiment

In a fourth embodiment of the invention, the invention is applied to single-crystal structure analysis when a predetermined kind of atoms included in a compound constituting a sample are partially substituted with another kind of atoms. The structure of the X-ray multiple spectroscopic analyzer 1 according to this embodiment is the same as the structure of the X-ray multiple spectroscopic analyzer 1 according to the first or second embodiment. When a part (some) of a predetermined kind of atoms included in a compound constituting a sample are substituted with another kind of atoms, the advantages of the invention can be better exhibited.

FIG. 17 is a diagram illustrating an example of a structure of a molecular model of a compound to be subjected to the single-crystal structure analysis according to this embodiment. The compound shown in the drawing is a sialon fluorescent material, is a material which can be made to emit light using a blue light-emitting diode, and is a material which can achieve a variety of white emission as a material of an LED illumination. The sialon fluorescent material used in the single-crystal structure analysis according to this embodiment is a compound which has a sialon of which the atom indicated by an arrow in the drawing is aluminum (Al) as a predetermined kind of atom in a basic chemical composition and in which a part (for example, 0.2%) of Al are substituted with europium (Eu). Here, a part of a predetermined kind of atoms (Al in this case) included in a compound are substituted with another kind of atoms (Eu in this case), it may be defined that the compound is doped with another atom. The ratio of the number of atoms Eu to be substituted to the total number of atoms Al of sialon before substitution is defined as an Eu substituted amount.

The sialon fluorescent material can be synthesized by solid-dissolving $Eu^{2+}$ ions in sialon. The substituent (doped) atom is not limited to Eu, but may be another rare-earth metal atom or another metal atom. The color formation can be controlled by controlling the Eu substituted (doped) amount. Accordingly, it is possible to emit various white colors such as cool daylight, daylight, cool white, warm white, and incandle light. The sialon fluorescent material is a next-generation illumination material which is superior in efficiency, durability and heat resistance and which has a suppressed environmental load in comparison with a mercury fluorescent lamp having a high environmental load. The sialon fluorescent material can be used, for example, as material of a backlight of a liquid crystal display.

The Eu substituted (doped) amount in the sialon fluorescent material can be controlled by controlling the amount of $Eu^{2+}$ ions to be solid-dissolved in the sialon, but the substituted (doped) amount may be uneven in plural crystal grains to be formed and thus it is difficult to accurately identify the Eu substituted amount in the sialon fluorescent material. Even in this case, since the measurement can be performed on one crystal as a sample by employing the invention, it is possible to more accurately determine the amount of another atom substituted in the sample.

When the Eu substituted amount is several %, an average structure is visible even through the X-ray diffraction measurement using a single crystal of the sialon fluorescent material as a sample, and it is thus difficult to determine the Eu substituted amount from the X-ray diffraction analysis. However, even when the Eu substituted amount is unknown before the measurement, the information on the chemical composition of the sample can be obtained through the use of the X-ray fluorescence analysis and it is thus possible to determine the Eu substituted amount. Therefore, similarly to the third embodiment, it is possible to more accurately analyze the single-crystal structure by using the result of the X-ray fluorescence analysis in the single-crystal structure analysis. By employing the X-ray multiple spectroscopic analyzer 1 according to the invention, the X-ray diffraction measurement and the X-ray fluorescence measurement can be performed in parallel, the X-ray fluorescence analyzing unit 24 of the control and analysis unit 9 can perform the X-ray fluorescence analysis, the structural analysis data analyzing unit 22 can determine the Eu substituted amount from the X-ray fluorescence analysis data output from the X-ray fluorescence analyzing unit 24, and the single-crystal structure analysis can be performed on the basis of the determined amount of Eu substituted, thereby determining the crystal structure of the sample. Particularly, when the wavelength of the characteristic X-ray of an atom of interest is close to the wavelength of the characteristic X-ray of Pb, the advantages of the invention can be better exhibited by employing the X-ray multiple spectroscopic analyzer 1 according to the second embodiment. Here, the Eu substituted amount is set to 0.5%, but is not limited to this value. Particularly, when the amount of another atom substituted is equal to or less than 10%, it is very difficult to determine the amount of another atom substituted through the use of the X-ray diffraction analysis. Accordingly, when the amount of another atom substituted is equal to or less than 10%, the advantages of the invention become marked.

Although the single-crystal structure analysis which can provide the marked advantages of the invention has been described in the third and fourth embodiments, the invention is not limited to this single-crystal structure analysis. The invention can be widely applied to single-crystal structure analysis for which it is advantageous to use the result of the X-ray fluorescence analysis.

What is claimed is:

1. An X-ray multiple spectroscopic analyzer comprising:
an X-ray source radiating X-rays;
an optical system inputting the X-rays radiated from the X-ray source to a single-crystal sample;
a sample stage supporting the single-crystal sample, with one or more rotation driving systems for rotating the single-crystal sample;
an X-ray diffraction detector detecting diffracted X-rays generated from the single-crystal sample;
a rotation driving system changing the angle of the X-ray diffraction detector with respect to the single-crystal sample;
an X-ray diffraction measurement data storage unit for storing measurement data of the diffracted X-rays detected by the X-ray diffraction detector;
a structural analysis data analyzing unit for analyzing data of a crystal structure on the basis of the measurement data of the diffracted X-rays stored in the X-ray diffraction measurement data storage unit;
an energy-dispersive X-ray fluorescence detector detecting fluorescent X-rays radiated from the single-crystal sample;
an X-ray fluorescence measurement data storage unit storing measurement data of the fluorescent X-rays detected by the energy-dispersive X-ray fluorescence detector;
an X-ray fluorescence analyzing unit for analyzing the fluorescent X-rays on the basis of the measurement data of the fluorescent X-rays stored in the X-ray fluorescence measurement data storage unit;
a beam stopper, being disposed opposite to the optical system about the single-crystal sample and blocking a direct beam of X-rays input to the single-crystal sample from the optical system;
an X-ray fluorescence analysis data storage unit for storing analysis data of the fluorescent X-rays output from the X-ray fluorescence analyzing unit; and
X-ray fluorescence analysis data acquiring unit for acquiring the analysis data of the fluorescent X-rays stored in the X-ray fluorescence analysis data storage unit and outputting the acquired X-ray fluorescence analysis data to the structural analysis data analyzing unit,
wherein the structural analysis data analyzing unit analyzes the data of the crystal structure further on the basis of the analysis data of the fluorescent X-rays output from the X-ray fluorescence analysis data acquiring unit, and
wherein the energy-dispersive X-ray fluorescence detector comprises
a light-receiving portion receiving the detected X-rays, and
an X-ray blocking member, being disposed between the beam stopper and the light-receiving portion and blocking fluorescent X-rays radiated from a part of the beam stopper which is directly irradiated with the direct beam.

2. The X-ray multiple spectroscopic analyzer according to claim 1, wherein the X-ray blocking member surrounds the peripheral edge of the light-receiving portion.

3. The X-ray multiple spectroscopic analyzer according to claim 2, wherein the X-ray blocking member has a tip formed in a tapered shape.

4. The X-ray multiple spectroscopic analyzer according to claim 2, wherein the X-ray blocking member includes a hollow light-guiding tube therein and functions as a poly-capillary.

5. The X-ray multiple spectroscopic analyzer according to claim 1, wherein the light-receiving portion of the energy-dispersive X-ray fluorescence detector is disposed on the optical system side about a plane perpendicular to the optical axis of a direct beam of X-rays input to the single-crystal sample from the optical system and passing through the single-crystal sample.

6. The X-ray multiple spectroscopic analyzer according to claim 1, wherein the energy-dispersive X-ray fluorescence detector further includes a retreating mechanism that can retreat outward from the single-crystal sample.

7. The X-ray multiple spectroscopic analyzer according to claim 1, wherein the energy dispersive X-ray fluorescence detector detects a posture where the sample stage supports the single-crystal sample by detecting the fluorescent X-rays radiated from the single-crystal sample.

8. The X-ray multiple spectroscopic analyzer according to claim 1, wherein the energy dispersive X-ray fluorescence detector is a silicon drift detector or a lithium-drift silicon detector.

9. The X-ray multiple spectroscopic analyzer according to claim 1, wherein the energy dispersive X-ray fluorescence detector detects the fluorescent X-rays radiated from the single-crystal sample in a first period which is a partial period of a period in which the X-ray diffraction detector detects the diffracted X-rays generated from the single-crystal sample.

10. The X-ray multiple spectroscopic analyzer according to claim 9, wherein the X-ray fluorescence analyzing unit analyzes the fluorescent X-rays on the basis of the measurement data of the fluorescent X-rays, which is detected by the energy dispersive X-ray fluorescence detector in the first period, in a second period which is a partial period of the period in which the X-ray diffraction detector detects the diffracted X-rays generated from the single-crystal sample and which is subsequent to the first period.

11. The X-ray multiple spectroscopic analyzer according to claim 1, wherein when a predetermined atom included in a compound constituting the single-crystal sample has a possibility of a plurality of kind of atoms, the structural analysis data analyzing unit determines the predetermined atom from the analysis data of the fluorescent X-rays and determines the crystal structure of the single-crystal sample on the basis of the determined atom.

12. The X-ray multiple spectroscopic analyzer according to claim 1, wherein when a part of a predetermined kind of atoms included in a compound constituting the single-crystal sample are substituted with a different kind of atoms, the structural analysis data analyzing unit determines an amount of the different atom from the analysis data of the fluorescent X-rays and determines the crystal structure of the single-crystal sample on the basis of the substituted amount.

* * * * *